(12) United States Patent
Medoff et al.

(10) Patent No.: US 7,195,633 B2
(45) Date of Patent: Mar. 27, 2007

(54) FRACTURE FIXATION SYSTEM

(75) Inventors: Robert J. Medoff, 30 Aulike St., Suite 506 Kailua, HI (US) 96734; Lars G. Tellman, Kyrkogatan 6, S-23011 Falsterbo (SE)

(73) Assignees: Robert J. Medoff, Kailua, HI (US); Lars G. Tellman, Falsterbo (SE); David Medoff, Valencia, CA (US)

( * ) Notice: Subject to any disclaimer, the term of this patent is extended or adjusted under 35 U.S.C. 154(b) by 257 days.

(21) Appl. No.: 10/754,462

(22) Filed: Jan. 8, 2004

(65) Prior Publication Data

US 2005/0154392 A1   Jul. 14, 2005

(51) Int. Cl.
*A61B 17/56* (2006.01)
(52) U.S. Cl. ..................................... 606/69
(58) Field of Classification Search ............. 606/61, 606/65, 66, 69, 70, 71, 73
See application file for complete search history.

(56) References Cited

U.S. PATENT DOCUMENTS

| 4,388,921 | A | * | 6/1983 | Sutter et al. ............... 606/71 |
| 5,053,036 | A | * | 10/1991 | Perren et al. ............ 606/69 |
| 5,607,426 | A | * | 3/1997 | Ralph et al. ............... 606/61 |
| 5,647,873 | A | * | 7/1997 | Errico et al. .............. 606/61 |
| 5,954,722 | A | * | 9/1999 | Bono ...................... 606/61 |
| 6,235,033 | B1 | * | 5/2001 | Brace et al. ............... 606/69 |
| 6,358,250 | B1 | | 3/2002 | Orbay |
| 6,364,882 | B1 | | 4/2002 | Orbay |
| 2002/0143338 | A1 | | 10/2002 | Orbay et al. |
| 2002/0143341 | A1 | * | 10/2002 | Biedermann et al. ........ 606/73 |
| 2003/0083660 | A1 | | 5/2003 | Orbay |
| 2003/0083661 | A1 | | 5/2003 | Orbay et al. |
| 2003/0105461 | A1 | | 6/2003 | Putnam |
| 2005/0251137 | A1 | * | 11/2005 | Ball ...................... 606/61 |

* cited by examiner

*Primary Examiner*—Eduardo C. Robert
*Assistant Examiner*—Michael J. Araj
(74) *Attorney, Agent, or Firm*—Ladas and Parry LLP

(57) ABSTRACT

A fracture fixation system in which a plate is secured to stable bone and posts are inserted at varying angles into an unstable bone fragment by engaging in rotatable bearings which are fixedly secured in the plate when the posts are fully engaged in the bone fragment. The bearings are formed as truncated spherical members having a number of longitudinal slots extending partway along the length of the bearing to form petals which are expanded outwardly when the posts are advanced in the bearing to produce non-uniform distribution of forces between the bearing and the plate which generate force couples to resist angulation of the posts and loss of fracture fixation. Various other ways of producing non-uniform force distribution are described.

74 Claims, 15 Drawing Sheets

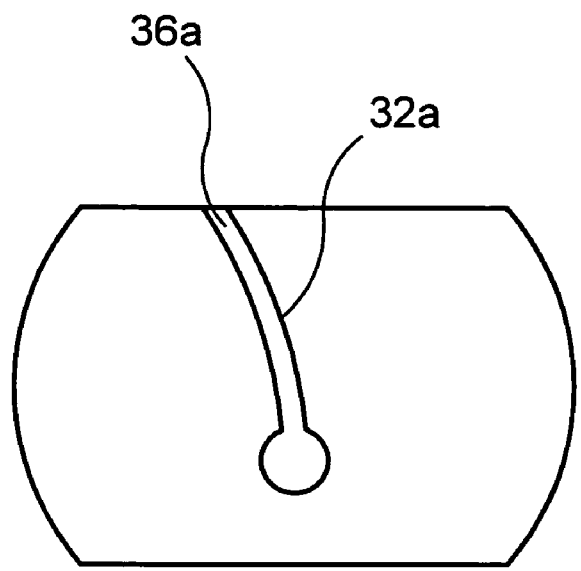
F I G. 5a
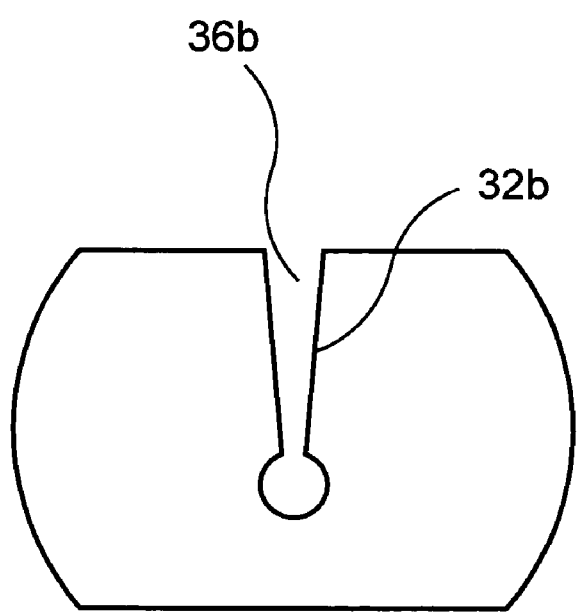
F I G. 5b

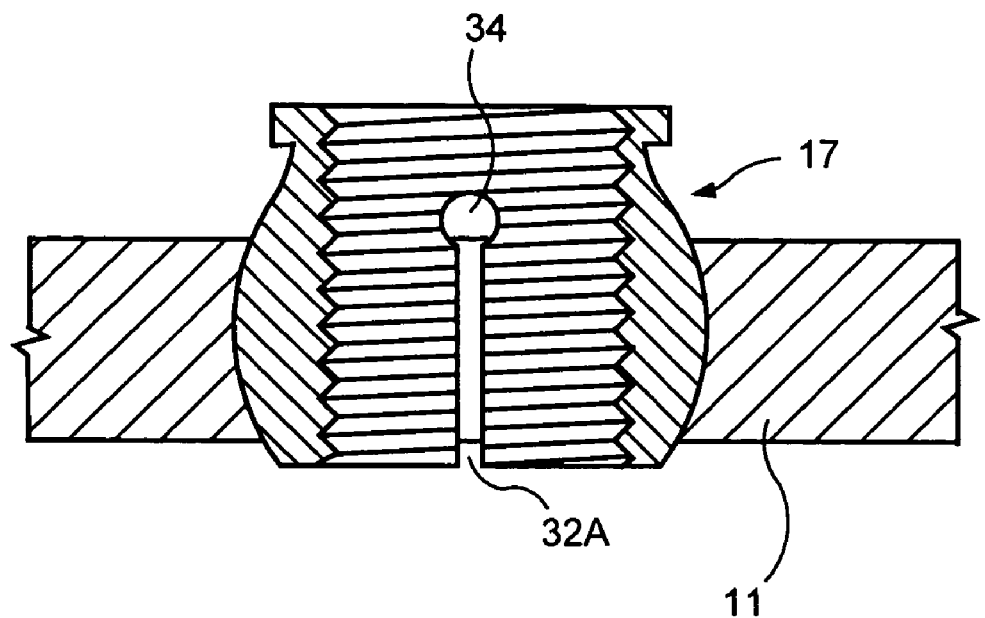
F I G. 11
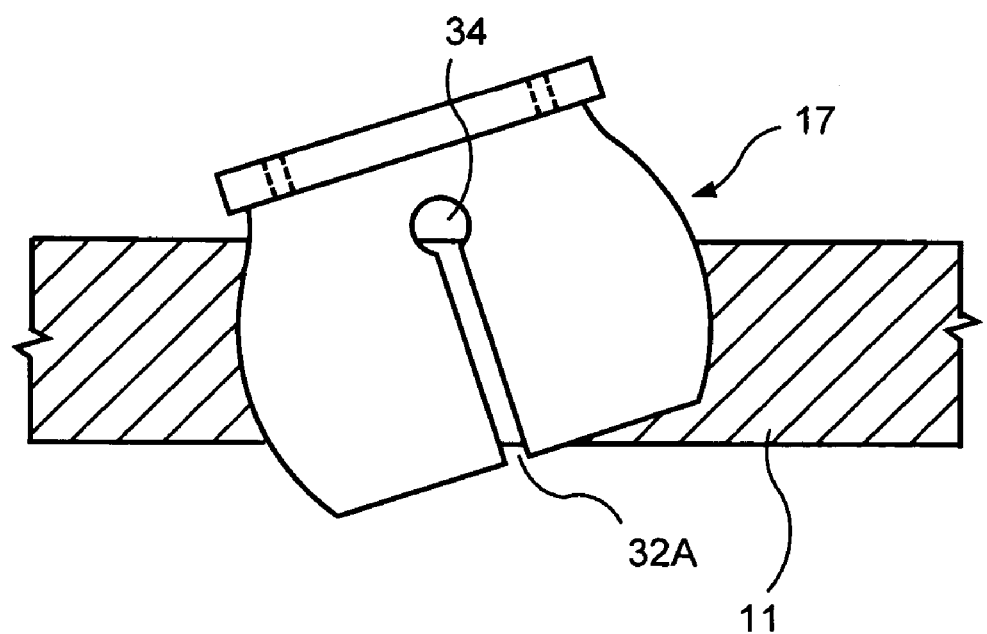
F I G. 12

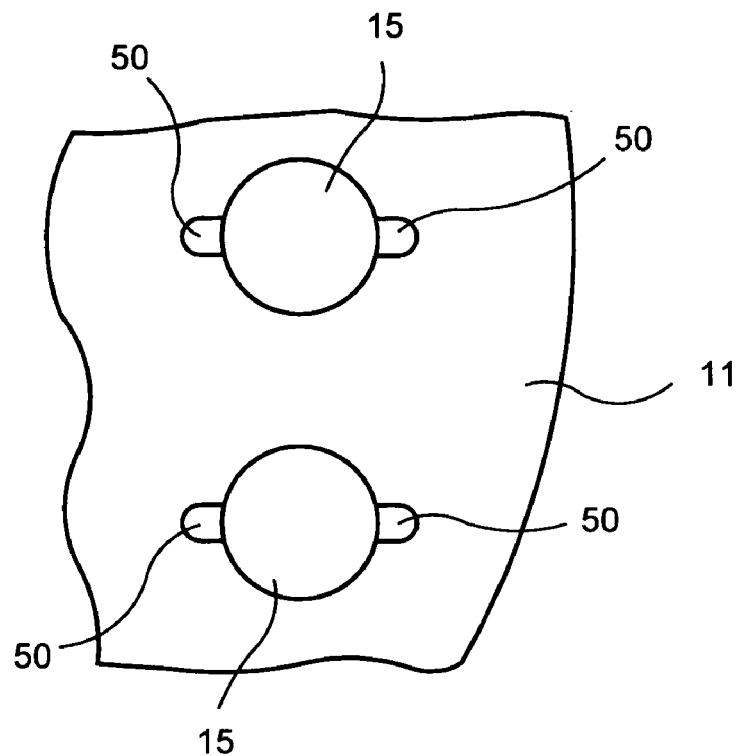
F I G. 13
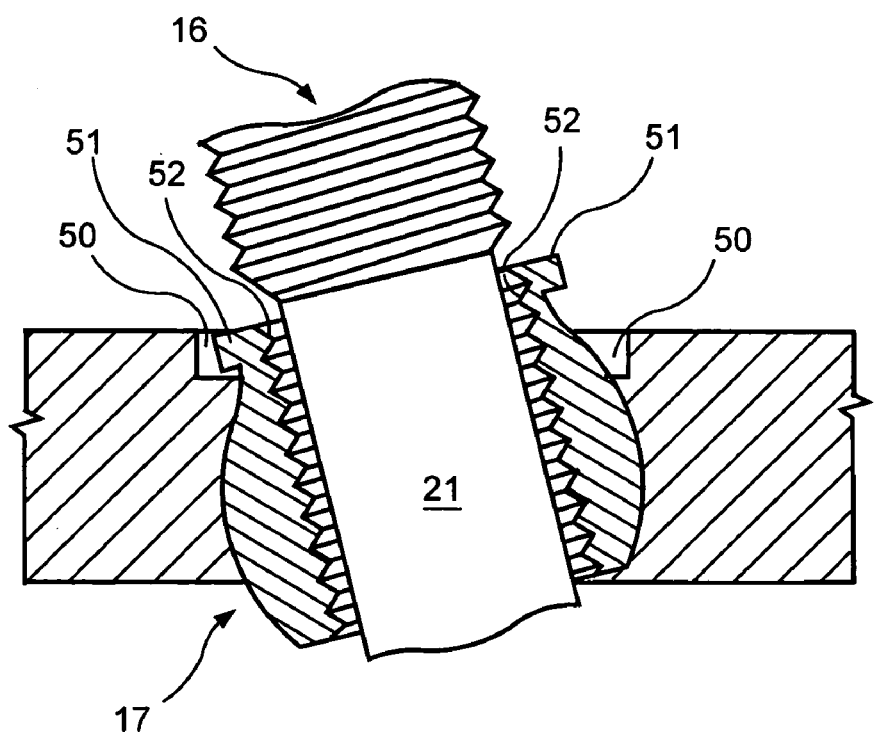
F I G. 14

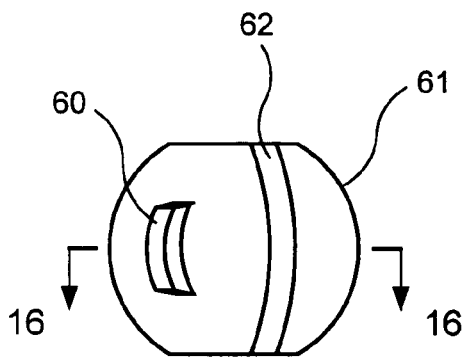
F I G. 15
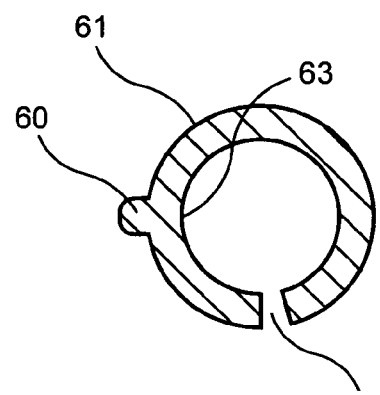
F I G. 16
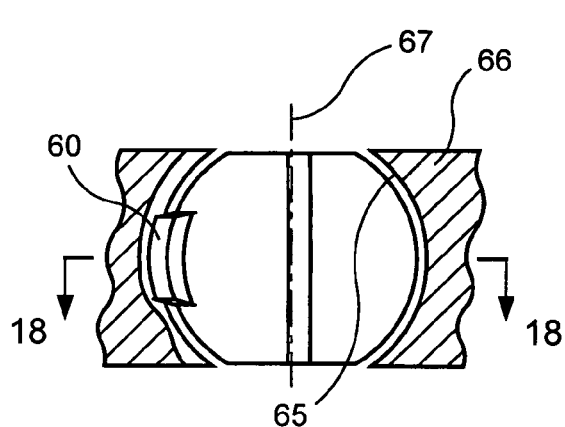
F I G. 17
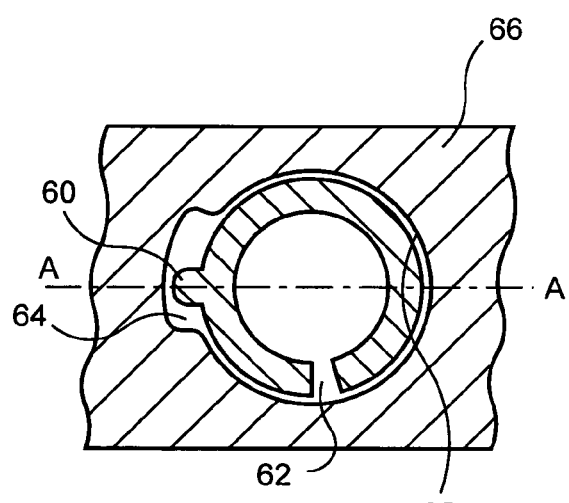
F I G. 18
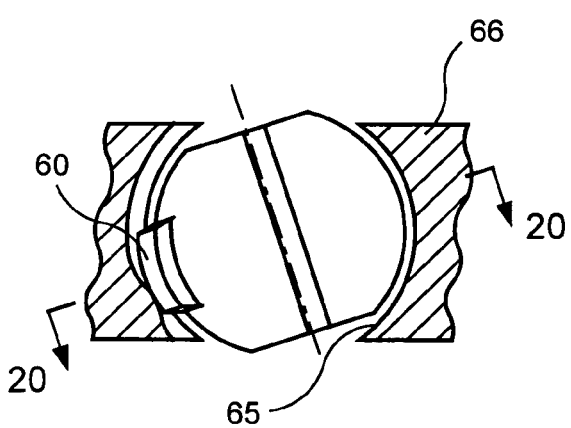
F I G. 19
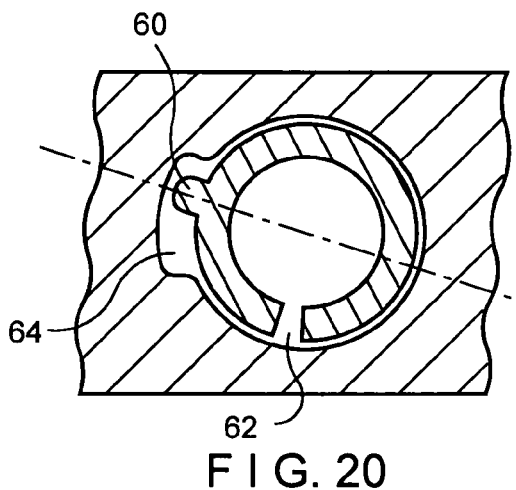
F I G. 20

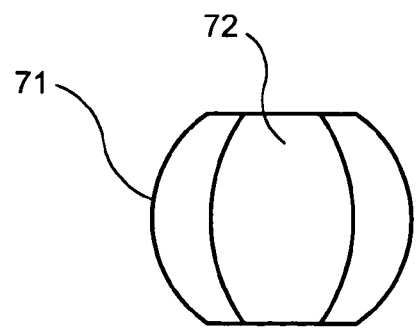
F I G. 21
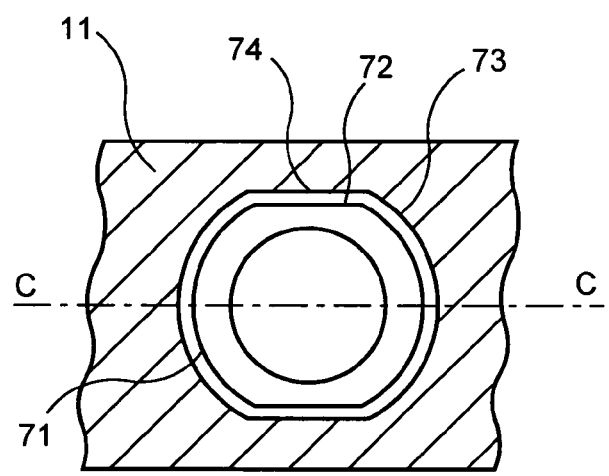
F I G. 22
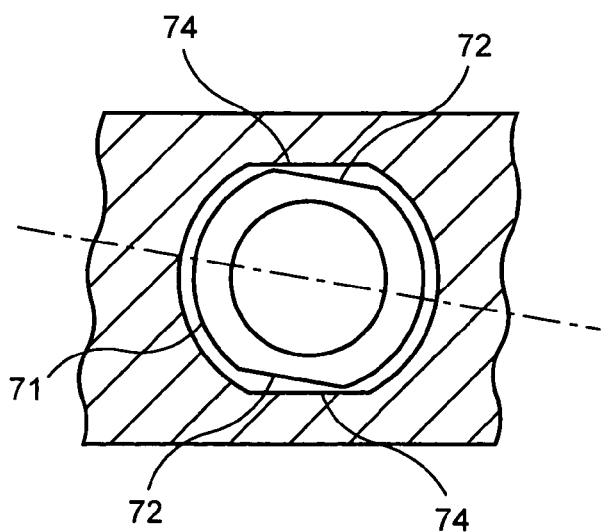
F I G. 23

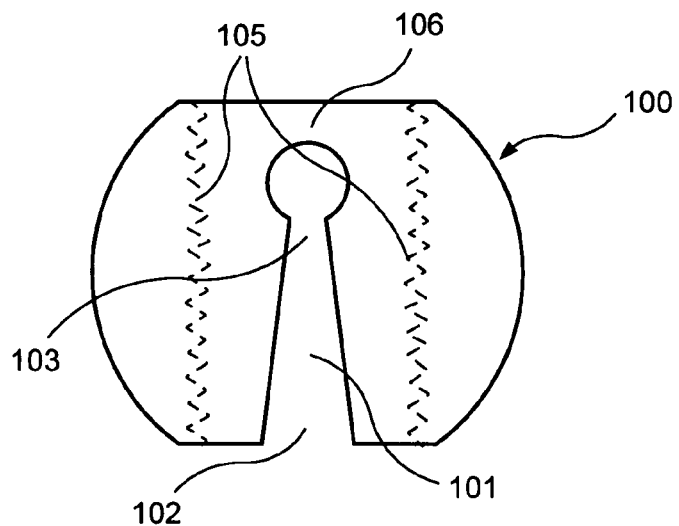
F I G. 24
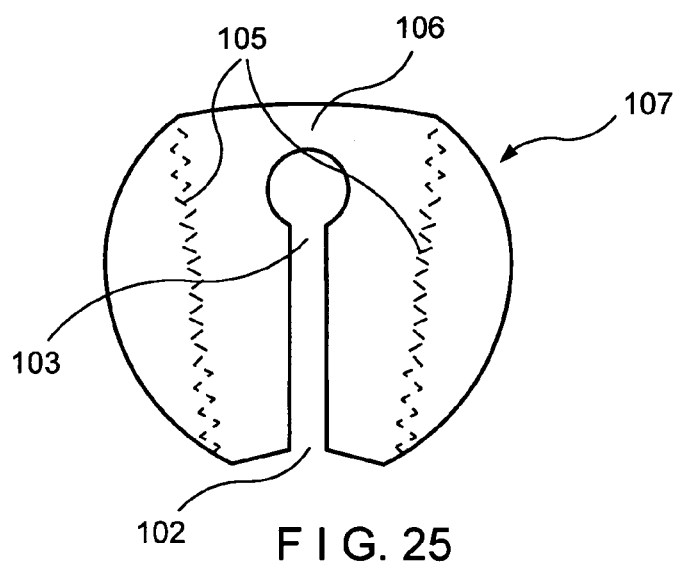
F I G. 25
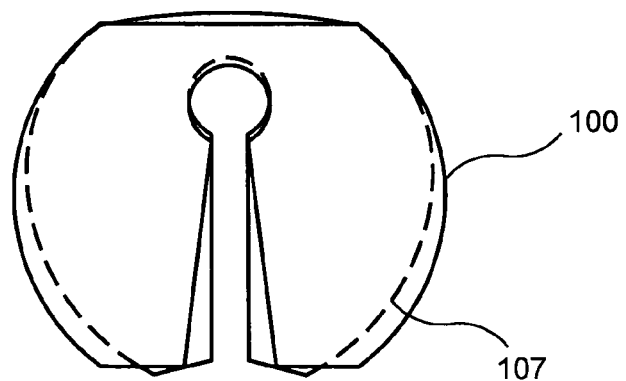
F I G. 26

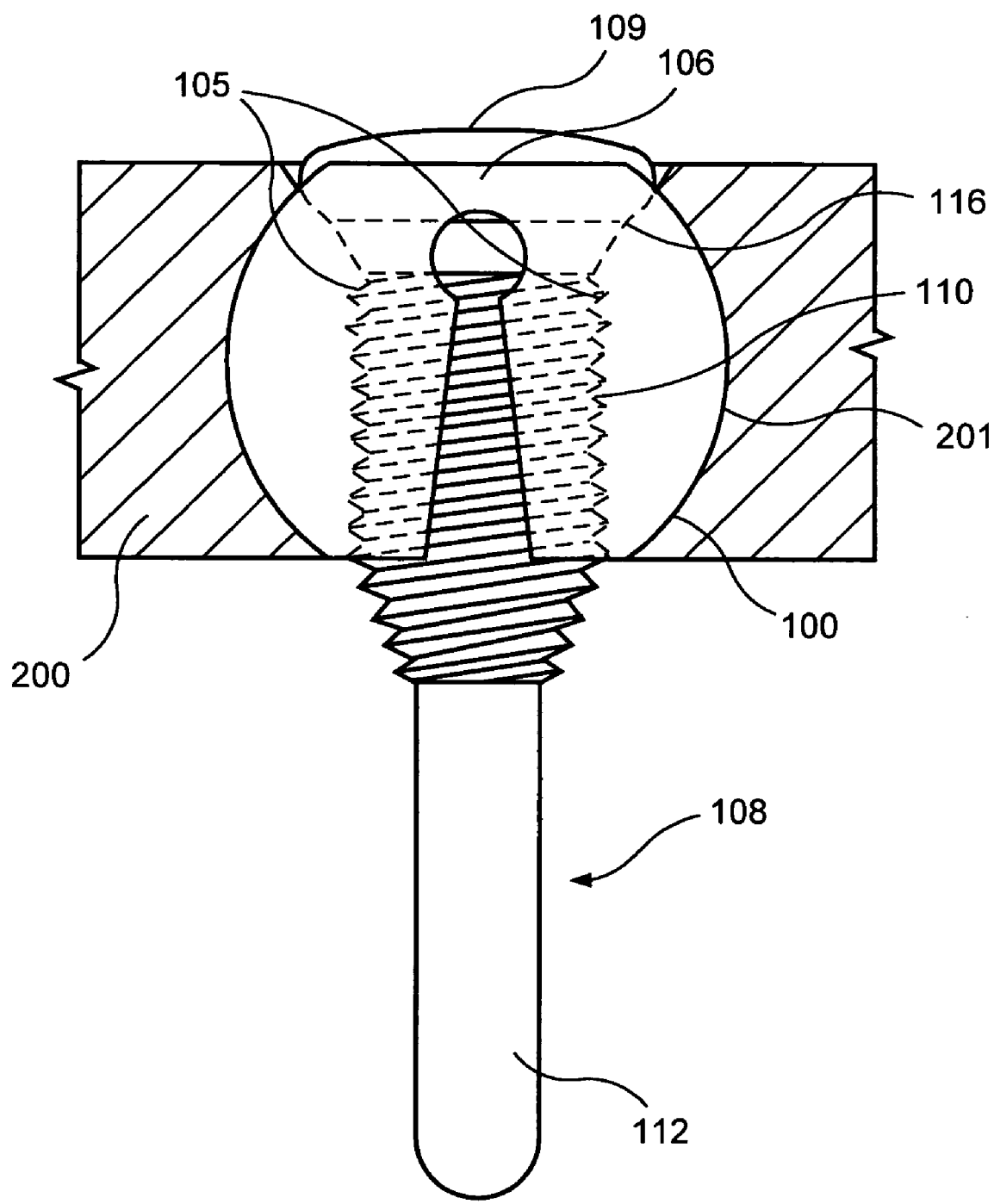
F I G. 28

FRACTURE FIXATION SYSTEM

FIELD OF THE INVENTION

The invention relates to a fracture fixation system in which a post is secured in a bone fragment and is locked in an adjustably angulated position in a plate secured to stable bone.

The invention further relates to the construction of a bearing which is disposed in the plate and which locks the post in the plate as the post is inserted in the bearing.

The invention further relates to a method for securing a post in an angulated position in a bearing in turn secured in a hole in a plate.

BACKGROUND AND PRIOR ART

Fixation of fractures near an articular surface are often fixed with devices, such as a buttress plate in order to support the articular surface from displacing. These devices share several common features: nearly all are manufactured as a plate which has fixation of the central fragment with one or more bone screws and provide fixation of the peri-articular fragment with one or more supporting tines, posts, or locked screws.

One such device is shown in published U.S. application 20030105461 (Putnam) and comprises a plate with fixed tines that extend at an angle to the plane of the plate. These tines are contiguous with the plate and extend at a fixed angle. A disadvantage of this construction is that the tines are located at fixed positions and the surgeon must implant all of them. Often the geometry of the fracture is such that the location of the tines is not optimally positioned and may enter a fracture site or protrude into the joint.

Another device includes plates that have fixed screws or posts that are screwed into a threaded hole in the plate. Also known, as shown in Orbay U.S. Pat. No. 6,358,250, are plates in which the posts or screws are inserted at varying angles. These constructions require that the head of the post or screw have enough thread purchase on the threads in the hole of the plate; this requires the plate to have sufficient thickness to allow an adequate number of threads for fixation of the post or screw. In addition, these plates require the post or screw to be inserted at a predefined angle.

A further device is shown in Orbay U.S. Pat. No. 6,364,882 and U.S. Publ. Appln. 2002/0143338 wherein the post or screw is provided with a partial spherical head so that it can be placed at a variable angle in the plate, and thereafter secured with a set screw. The spherical head is provided with slots to facilitate its expansion into the hole when it is secured by the set screw. Although this construction allows greater flexibility for inserting the post at a variable angle, it requires even more thickness for the plate in order to compensate for the thickness of the post or screw head in the plate hole as well as providing a sufficient number of threads for purchase by the set screw. In addition, since the set screw only compresses the head of the post or screw over a fairly small surface area, the frictional forces generated are relatively small whereby there is a risk of inadequate fixation of the post or screw and subsequent postoperative angulation and loss of reduction. In addition, this system is cumbersome to use because of the need for the surgeon to manipulate a small set screw behind the post or screw head, resulting in increased difficulty in surgical technique. Finally, because the head of the fixation post is slotted, it creates an area of considerable weakness where the shaft of the post connects to the slotted head. This is subject to considerable torque and is prone to breakage.

Another device is shown in U.S. Pat. No. 5,954,722 (Bono) wherein a split bushing is engaged in a plate and receives a bone screw which expands the bushing and frictionally locks the bushing in the plate. Although this configuration is useful to compress the head of the post to prevent it from backing out, it does not produce a large surface area of contact between the bushing and the surface of the hole. The bushing is narrow and has a spherical radius that is slightly smaller than that of the hole in order to allow initial rotation of the bushing in the hole to orient the screw. As the bone screw head expands the bushing cylindrically, contact of the bushing with the surface of the hole in the plate is primarily restricted to a narrow zone of contact along a single equatorial plane of the bushing since the curvature of the bushing along its principal axis is more pronounced than that of the hole. Although this configuration generates compressive forces on the head of the screw to prevent it from backing out, if forces on the bone fragment generate torque on the post, the resistance to torque is limited to the frictional forces generated from this limited plane of contact of the bushing along the equatorial zone. The device is intended for use in stabilizing multiple vertebrae in the spinal column and the frictional forces are intended to prevent the screws from backing out of the plate but they are not intended to nor are they sufficient to resist torque imposed on the screws by shifting of an unstable bone fragment of a fracture.

Another limitation of the device in U.S. Pat. No. 5,954,722 (Bono) is that the bushing allows variation of the insertion angles within a predefined conical range. However, there are clinical situations in which it is desirable to limited the range of insertion angles primarily along a single plane. For instance, in some situations it may be desirable to allow variation along an axis from proximal to distal, but limit variation from side to side so that the post will not penetrate the joint or other important structures.

Another limitation of the device in U.S. Pat. No. 5,954,722 (Bono) is that the bushing tends to spin as the post head is inserted. As the size of the bearing is reduced, it becomes increasingly difficult to insert the post fully since the bearing spins before sufficient expansion has occurred to generate large frictional forces.

SUMMARY OF THE INVENTION

An object of the invention is to provide a fracture fixation system which avoids the problems described above and by which reliable and simple securing of the post or screw in the plate is obtained.

The fixation system comprises an implant based on a concept of providing an intermediate fixation element or bearing between the post or screw and the hole in the plate. The post is threaded into this intermediate element to cause threads on the post to produce expansion or displacement of the intermediate element against the hole in the plate. This intermediate element can be inserted into the plate hole before the plate is applied to the bone whereby no manipulation of cumbersome small set screws is required. Moreover, since the compression of the intermediate element is through the periphery or surface of the plate hole, a wider surface area for compression is obtained resulting in greater resistance to torque. Since the threads are distributed within the intermediate element, the plate does not have to be made excessively thick to allow enough thread purchase for fixation. Additionally, the construction of the invention allows the capability of placing the post or screw in a range of angles, either along two separate degrees of freedom (in a variety of conical positions) or varying primarily along a single degree of freedom (varying along a single plane as directed by the shape of the hole and the bearing).

Finally, since the head of the post is not split with a thin zone of connection to the shaft of the post, the risk of breakage of the post or screw from torque is greatly reduced.

The invention is characterized by forming the bearing in such a way to produce more than one zone of contact when the bearing is expanded, which provides greater resistance to torque applied to the post or screw by tendency of displacement of the bone fragment, after its fixation. By providing more than one zone of contact, a non-uniform distribution of radial forces is produced between the bearing and the plate to resist the applied torque in addition to friction forces. In addition, certain variations allow production of a force couple, providing improved resistance to applied torque.

More particularly, the bearing has an outer surface of spherical contour which can be angularly rotated in a spherical hole in the plate and the bearing is provided with one or more longitudinal slots extending from one pole of the bearing partially or completely along the length of the bearing to cause expansion to occur when the post or screw is engaged in the bearing which creates multiple areas of contact at the top and bottom of the bearing to improve resistance in applied torque on the post or screw by the bone fragment.

Another object of the invention is to restrict the range of insertion angles to a single plane, or a limited variation to either side of a single plane, in order to improve the resistance to torque applied to the post at right angles to the plane as well as restrict the possible insertion angles to a predefined range.

Another object of the invention is to provide means to overcome the problem of spinning of the bearing as the post is inserted into the bone in the bearing.

BRIEF DESCRIPTION OF THE FIGURES OF THE DRAWING

FIG. 5a shows a modification of the bearing of FIG. 5.

FIG. 5b shows another modification of the bearing of FIG. 5.

FIG. 11 shows the bearing of FIG. 8 in its initial loosely supported state in the plate.

FIG. 12 shows the bearing of FIG. 8 after its rotation in the plate.

FIG. 13 shows a portion of the plate in which the hole has been modified to prevent rotation of the bearing when the post is being installed.

FIG. 14 shows the bearing installed in the plate hole in FIG. 13.

FIG. 15 is an elevational view of another embodiment of the bearing according to the invention.

FIG. 16 is a sectional view taken along line 16—16 in FIG. 15.

FIG. 17 is an elevational view showing the bearing of FIG. 15 installed in a hole in the plate.

FIG. 18 is a sectional view taken along line 18—18 in FIG. 17.

FIG. 19 shows the bearing of FIG. 17 in an angularly adjusted position.

FIG. 20 is a sectional view taken on line 20—20 in FIG. 19.

FIG. 21 is an elevation view of another embodiment of the bearing.

FIG. 22 is a transverse sectional view of the bearing of FIG. 21 shown installed in a hole in the plate.

FIG. 23 shows the bearing of FIG. 22 in a slightly rotated limited position in the hole in the plate.

FIG. 24 is a side view of another embodiment of the bearing.

FIG. 25 shows the embodiment in FIG. 24 after it has been prestressed.

FIG. 26 shows the superimposed outline of the bearing shown in FIGS. 24 and 25.

FIG. 28 shows the bearing of FIG. 27 after it has been inserted into the plate and after seating of a post in the bearing.

DETAILED DESCRIPTION

The invention will be described hereafter with reference to fixation of a fracture of the radius of the wrist utilizing a fixation system which enables fixation of the fracture and which secures the fracture and resists forces tending to produce fracture displacement. As will be evident to those skilled in the art, the invention is applicable to other fractures as well, such as fractures of the fibula, the medial malleolus of the ankle, the distal end of the ulna, the humerus and the tibia.

Figure 1:
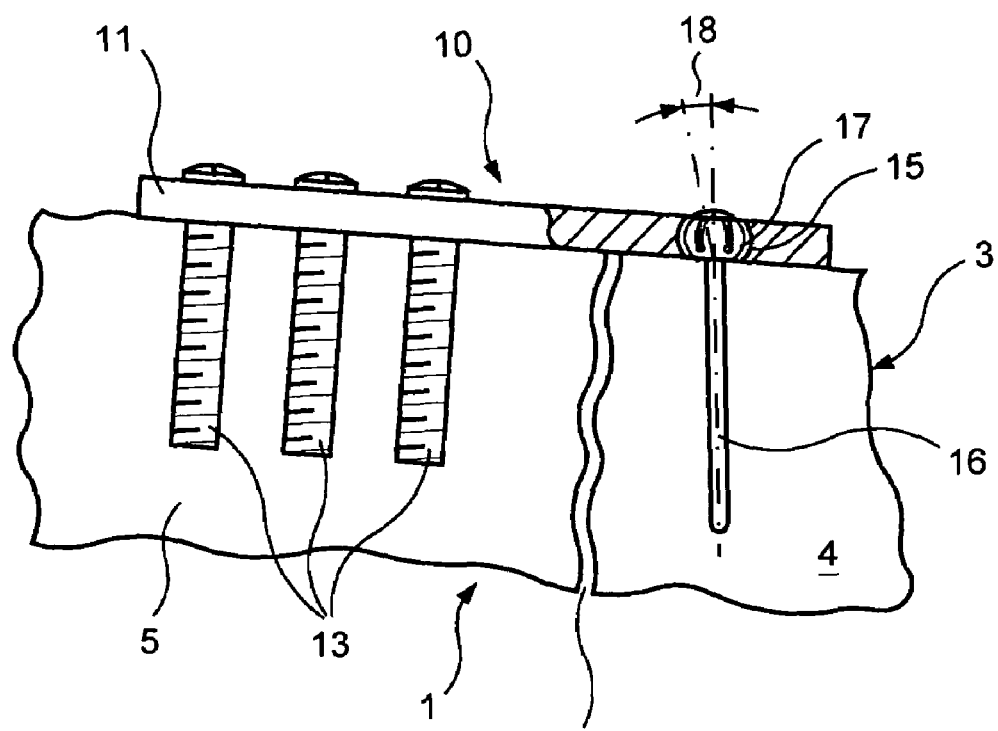
FIG. 1 is a diagrammatic sectional view illustrating the fracture fixation system of the invention.
Figure 2:
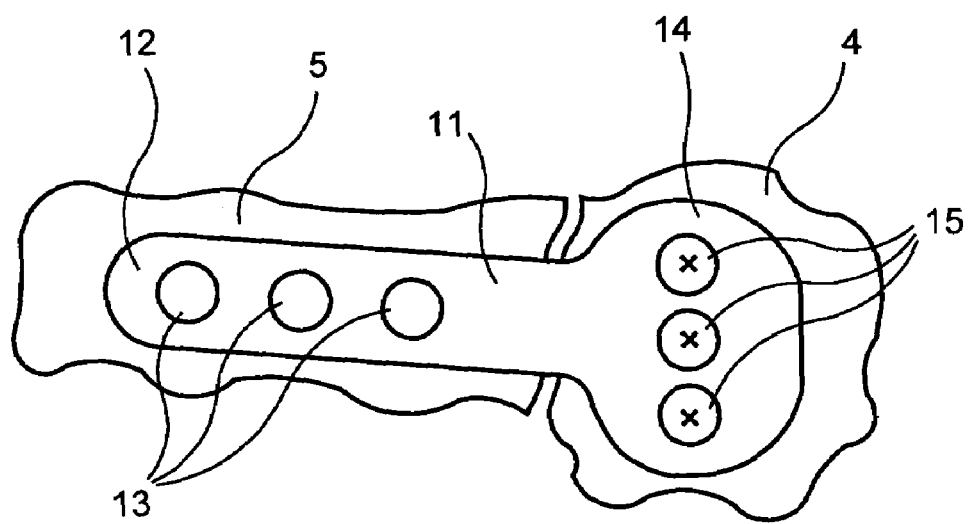
FIG. 2 is a top view thereof.

Referring to FIGS. 1 and 2, therein is shown, on enlarged scale, the distal end portion of the radius 1 of the wrist in which a fracture 2 is formed near the distal end 3. The fracture 2 defines an unstable distal bone fragment 4 and a stable proximal bone fragment 5.

Fixation of the fracture 2 is achieved with a fracture fixation system 10 which includes a plate 11 having a proximal portion 12 fixed to the stable bone fragment 5 by bone screws 13. The bone screws 13 may have smooth heads or threaded heads that lock into a threaded hole in the plate, the term screw being used to refer to either type of fixation. The plate 11 has a distal portion 14 having a number of spherical holes 15 in which are secured fasteners 16 which enter and are secured in the distal unstable bone fragment 4. The fasteners 16 can be in the form of pins, rods, wires or screws and hereafter will be referred to as posts. The posts 16 are supported in bearings 17 which are adjustably secured in the holes 15 in the plate to enable the posts 16 to be positioned at different angles 18 in the unstable fragment 4.

Figure 3:
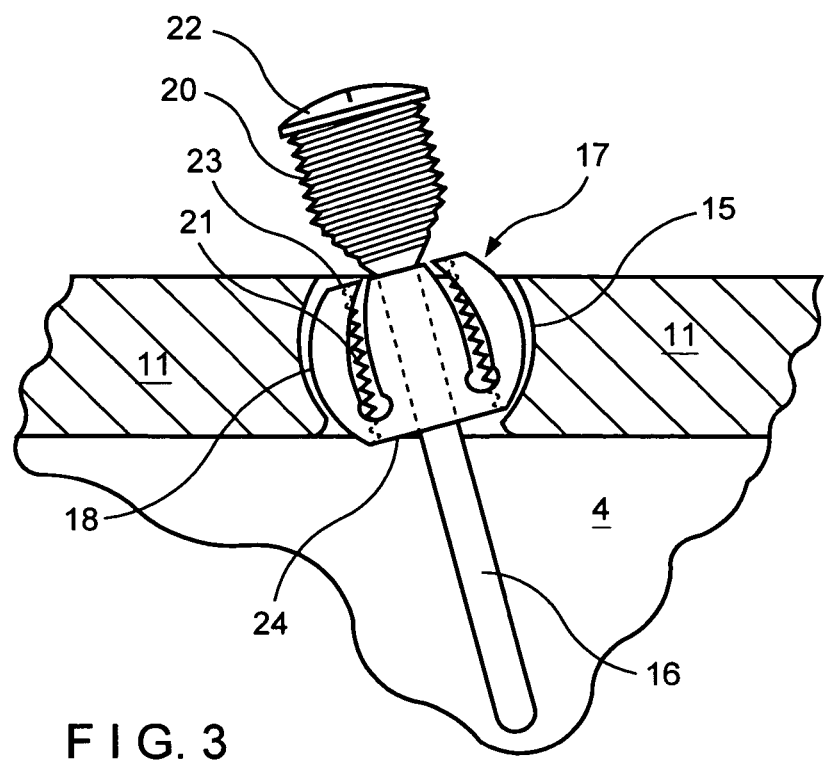
FIG. 3 shows a portion of the system in FIG. 1 in a first stage of installation thereof.
Figure 4:
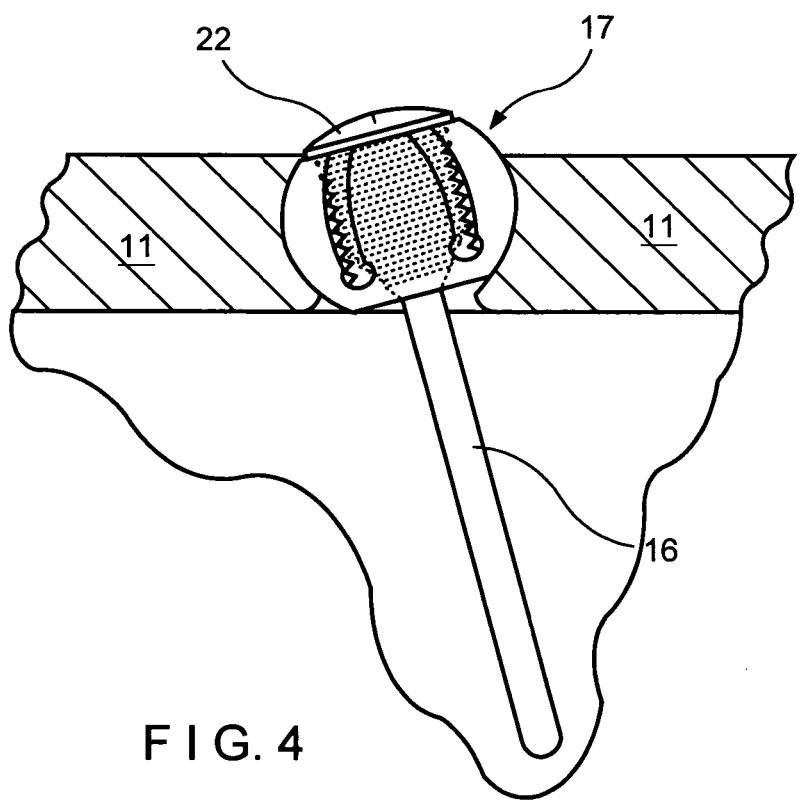
FIG. 4 shows the system in a completed stage of installation.

FIG. 3 shows the post 16 in a partially inserted state in the bearing 17 and the unstable fragment 4. FIG. 4 shows the post in a fully inserted position in which the bearing 17 is locked in the plate 11.

The bearing 17 has an outer surface 18 of spherical shape which fits in a respective hole 15 in plate 11. The hole 15 is of a corresponding spherical shape as the outer surface of the bearing to allow the capability of the bearing to turn in the hole. Accordingly, the bearing is freely turnable in all directions within the hole 15 in order to adjust the angle at which the post 16 is to be inserted into the fragment 4. The bearing 17 is provided with slots (as will be explained in detail later) so as to be outwardly expandable and become locked in hole 15. When the post is fully seated in the bearing, the bearing will be locked in the hole 15.

In order to obtain the expansion capability of the bearing 17 to lock the bearing in the hole 15, the post has a threaded portion 20 which engages a threaded bore 21 centrally located in the bearing which advances the post into the bearing. In one embodiment, the threaded portion 20 of the post is oversized so that when the threaded portion 20 of the post is threadably advanced in the threaded bore in the bearing, it will produce a radial expansion of the bearing to lock the bearing securely within the hole 15 in the plate 11. The threaded portion 20 may be tapered over its length in order to produce increasing amounts of expansion as the post is advanced. Alternatively, the threaded portion may have a uniform diameter over most of its length so that a predetermined amount of expansion will occur. In either embodiment, the threaded portion 20 may have a tapered region at the leading threads in order to make it easier to get started and prevent cross threading as the threaded portion 20 is inserted into the threaded bore 21.

In another embodiment, a head 22 at the end of the post is oversized relative to the threaded bore 21 such that the head of the post causes expansion at the upper open end of the bearing as the head is seated into the bearing. The head 22 enables the post to be turned in order to threadably advance the post in the bore in the bearing. The head 22 also limits the advance of the post in the bearing. The post 16 can be formed without head 22 and a slot can be formed at the top of the post for engagement by a tool to rotate the post and advance it into the bearing. In another embodiment in which the slots in the bearing extend from the bottom of the bearing either partially or completely to the top, the expansion mechanism can be formed by a reduced diameter of the lower end of the threaded bore 21 which corresponds to a shoulder at the lower end of the threaded region 20 of the post so as to cause expansion at the lower end of the bearing.

In FIGS. 3 and 4 the post is inserted initially into the open end of the bearing and the upper end of the post causes the expansion of the bearing as it is fully seated. Since the expansion occurs primarily at the open end 23 of the bearing rather than the closed end 24, the outer surface 18 becomes pear shaped rather than spherical as the expansion occurs. As will be shown subsequently, this creates two zones of contact at different levels of the plate hole 15 and improves torque resistance when forces are applied to the distal end of the post due to drift of bone fragment 4.

Moreover, the design in FIGS. 3 and 4 shows insertion in the bearing at the open end 23. The bearing could also be inverted in which case the post will be inserted into the closed end 24 and expansion generated by a conical thread on the lower end of the bore in the bearing.

Figure 5:
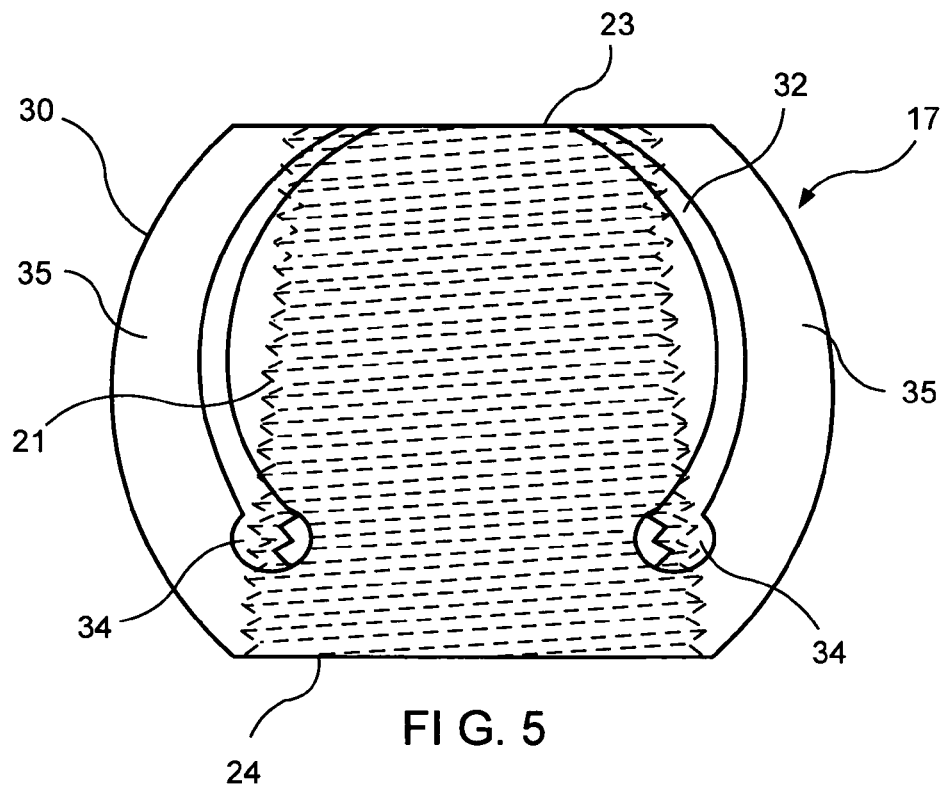
FIG. 5 is a side elevational view of a bearing of the fracture fixation system.
Figure 6:
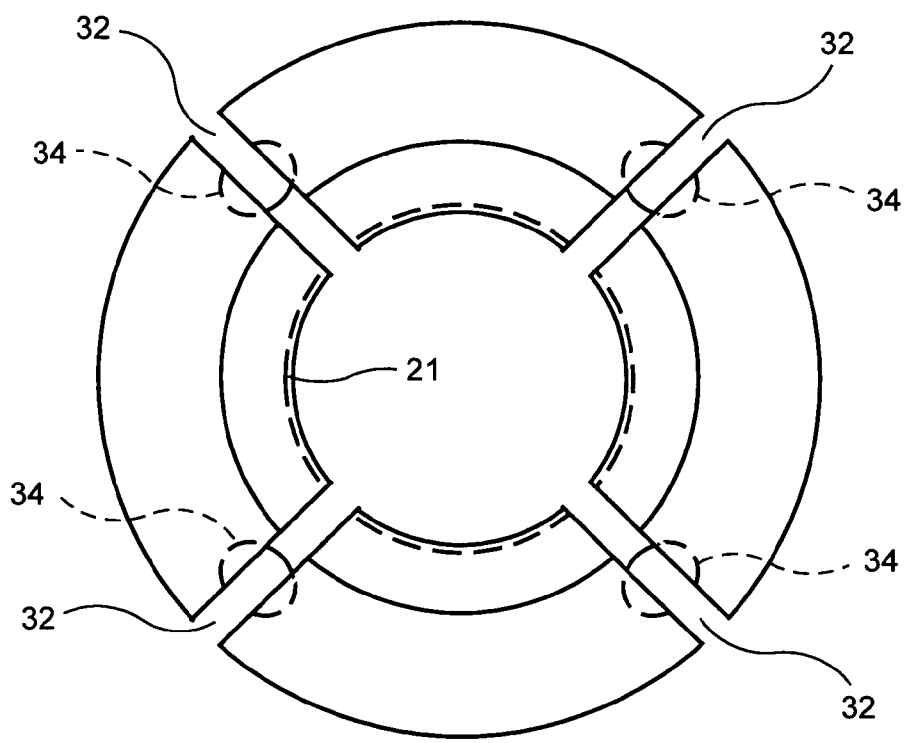
FIG. 6 is a top, plan view of the bearing.

FIGS. 5 and 6 illustrate a preferred embodiment of the invention respectively in elevation and plan views. The bearing 17 is formed as a body 30 of truncated spherical form. In order to confer radial expandability of the bearing 17, a plurality of slots 32 extend longitudinally along the length of the bearing, at equally spaced circumferential intervals, from the upper edge 33 of the bearing to a position more than halfway along the length of the bearing. Preferably, the slot extends *about* three-quarters of the length of the bearing. Although four slots have been shown in the embodiment of FIGS. 5 and 6, a greater or lesser number can be provided. The slots 32 extend from the upper end 23 of the bearing to provide a means by which the bearing will be locked securely in the plate as will be explained more fully later.

At the lower end of each slot 32, is an enlargement to provide stress relief to prevent cracking at the bottom of the slot. The enlargement can take numerous forms, such as a horizontal cut to form a T-shape enlargement. Preferably, the enlargement is in the form a hole 34 of diameter greater than the width of the slot which provides stress relief for the bearing at the bottom of the slot to prevent cracking when the bearing is expanded. The slots 32 define lever-like petals 35 circumferentially spaced around the bearing, which act as cantilever beams, to undergo opening as the post is threadably advanced in the threaded bore 21 of the bearing. The stress relief holes 34 also promote the expandability of the lever-like petals 35. In a particular embodiment, the post has a diameter of 0.117", and the truncated bearing has a diameter of 0.165" and a height of 0.100". The diameter of the bore in the bearing is substantially equal to the diameter of the post. The slots have a width of 0.032" and a length of 0.073". The stress relief hole at the end of each slot has a diameter of 0.040". The bearing is made of stainless steel or titanium. The dimensions expressed herein are only exemplary and will vary depending on particular use.

Figure 7:
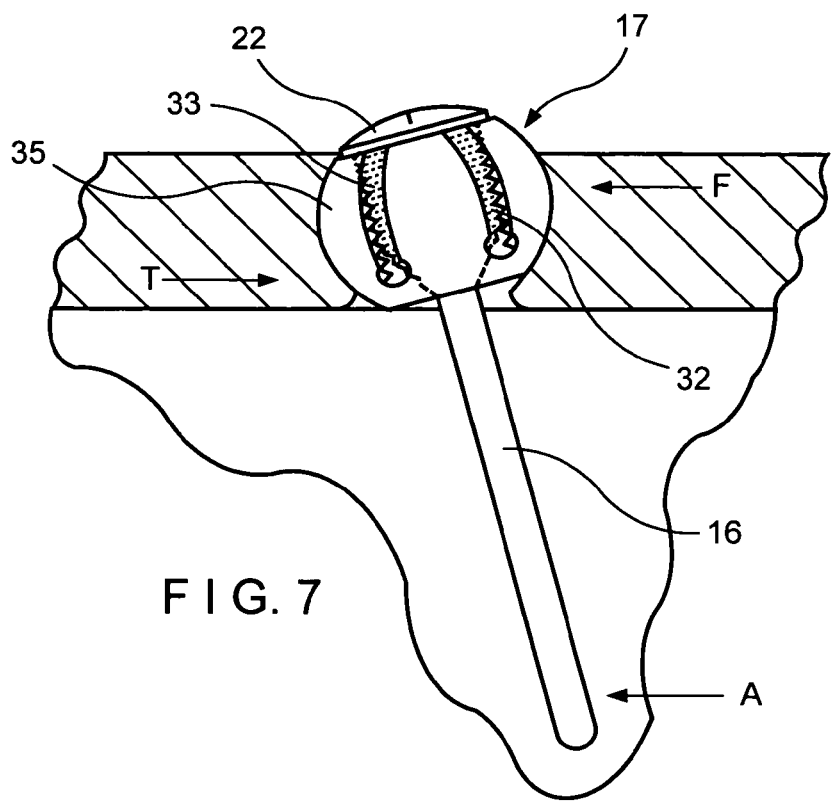
FIG. 7 is similar to FIG. 4 and shows the forces developed when the bearing is expanded.

FIG. 7 shows the forces acting between the bearing 17 and the plate 11 which serve to lock the bearing in the plate, when the post is threadably advanced in the bore of the bearing. Namely, as the post 16 is advanced in the bearing 17, the upper ends 33 of the lever-like petals 35 expand outwardly in the hole 15. This causes the bearing to be pushed down vertically trying to force it out of the bottom of the hole 15. When a load A is applied to the distal end of the post, the combination of the vertical displacement of the bearing in the hole and the pear shaped geometry of the expanded bearing produce a cam-like mechanism binding rotation of the bearing in the hole and generating reactive forces F and T which produce a resistant force couple. The forces F and T are non-co-linear and develop the force couple which tightly and securely locks the bearing in the plate hole 15. Conventional bearings which rely solely on frictional fit without the force couple may not adequately resist the torque applied to the posts by migration of the bone fragments after fracture fixation. When a solid or fully split spherical bearing is expanded cylindrically by a post, the main contact between the bearing and the surrounding hole is at the equator of the bearing which provides a limited frictional force generated from the relatively limited zone of contact between the bearing against the hole to resist the applied torque. Since the area of frictional contact is relatively small, the frictional forces are a fraction of the compressive forces F and T developed at the upper and lower surfaces as shown in FIG. 7, and relatively poor torque resistance is obtained. In the bearing of the present invention, the force couple developed by the two forces F and T, which are not co-linear, provides substantially higher resistance to the torque applied by loads from the unstable bone fragment into which the post has been inserted.

By virtue of the shape of the force applied by the post when introduced into the hole (along a cylindrical front) and the asymmetrical expansion of the petals of the bearing as cantilever beams, the contact between the petals of the bearing produces the non-colinear compression forces. The ensuing metal deformation between the bearing and the plate hole adds to the non-colinearity of the forces. The absence of contact in the central or equatorial region of the bearing further promotes the separation and non-colinearity of the developed compression forces. As a result, when torque is applied to the bearing due to torque applied to the post by drift of the unstable bone fragment, to which the post is secured, a reliable force couple is developed between the bearing and the plate hole to resist the torque applied to the post.

Figure 7A:
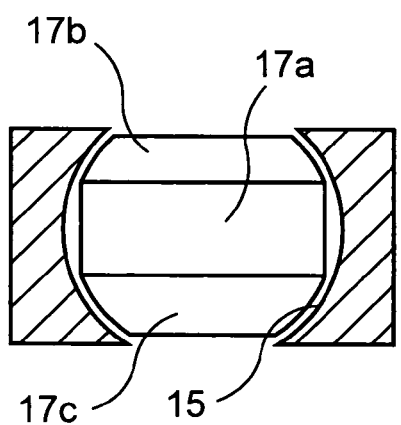
FIG. 7a is similar to FIG. 5 and shows a modification of the bearing therein.
Figure 7B:
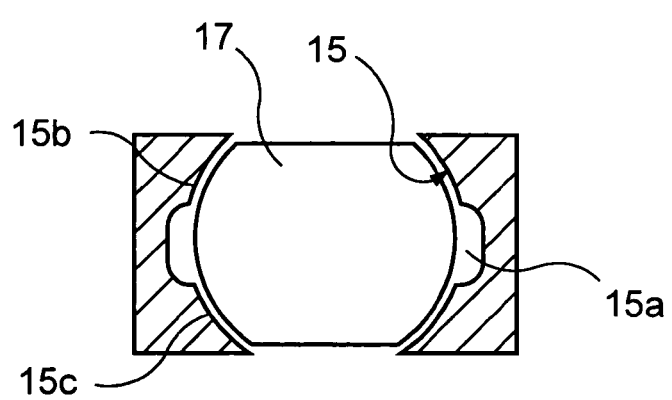
FIG. 7b is similar to FIG. 5 and shows another modification of the bearing therein.

FIGS. 7a and 7b show two alternative embodiments that improve the surface contact and torque resistance between the bearing and plate hole 15 as the bearing expands cylindrically. In order to assure that the zone of contact between the bearing and the plate hole 15 is not limited to a single equatorial plane, the hole in the plate can be formed so that the central or equatorial region of the bearing will not contact the plate, whereby contact at the plate hole 15 will occur at two planar zones of contact at both the upper end and the lower end of the bearing, greatly increasing the surface area of contact and resistance to applied torque. In FIG. 7a the central or equatorial region 17a of the bearing is flattened all around so that contact of the bearing with hole 15 is achieved in contact regions 17b and 17c. In FIG. 7b a central or equatorial region 15a of hole 15 is recessed so that only upper and lower portions 15b and 15c of the hole 15 make contact with the bearing 17.

The arrangements in FIGS. 7a and 7b develop two rings of contact above and below the equatorial region of the bearing, increasing the surface area of contact as well as generating forces that are distributed non-uniformly across the thickness of the plate to resist torque.

While the sides of the slots 32 have been shown straight and parallel in vertical planes, it is also possible to make the slots curved or angled as shown at 32a in FIG. 5a and to make the slots widen as shown at 32b in FIG. 5b. The curved and widened slots 32a and 32b provide edges of acute angle shape as shown at 36a and 36b which tend to deform more as the post is installed in the bearing and can bite into the wall of the plate hole to enhance the compressive force and the engagement of the top of the petals in the bearing hole.

Figure 8:
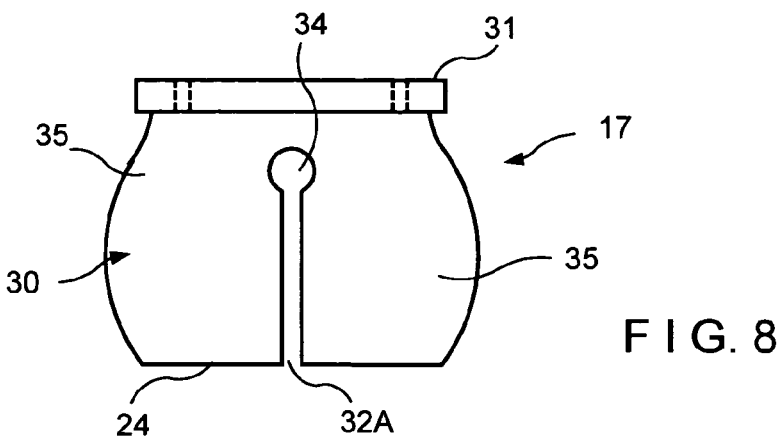
FIG. 8 is a side elevational view of another embodiment of the bearing.
Figure 9:
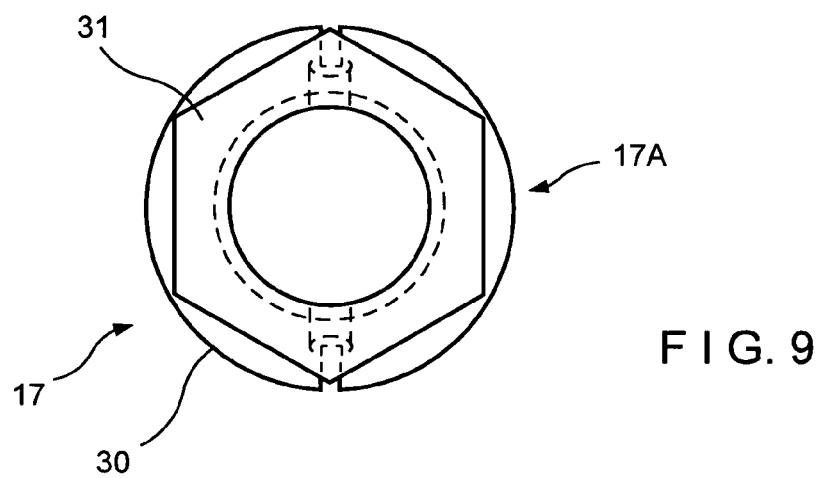
FIG. 9 is a view of the bearing of FIG. 8 from below.

FIGS. 8 and 9 show another embodiment of the bearing in elevation and plan views. The body 30 of bearing 17 has a head 31 at its upper end. The head 31 has a hexagonal shape in order to be engaged by a tool such as a wrench so as to be held against spinning when the post is threadably advanced in the threaded bore 21 (see FIG. 3) in the bearing. The head 31 is optional and the bearing may be held against spinning by friction with the wall of the plate hole 15 or tabs as will be explained later.

In FIGS. 8 and 9, two slots 32A are shown which extend from the lower end 24 of the bearing upwardly along the length of the bearing and terminate at relief holes 34. The expansion mechanism is the same as in FIGS. 5 and 6 except that it is the lower ends of the petals 35 which are forced outwards when the bearing is expanded. A similar force couple is produced as shown in FIG. 7.

Figure 10:
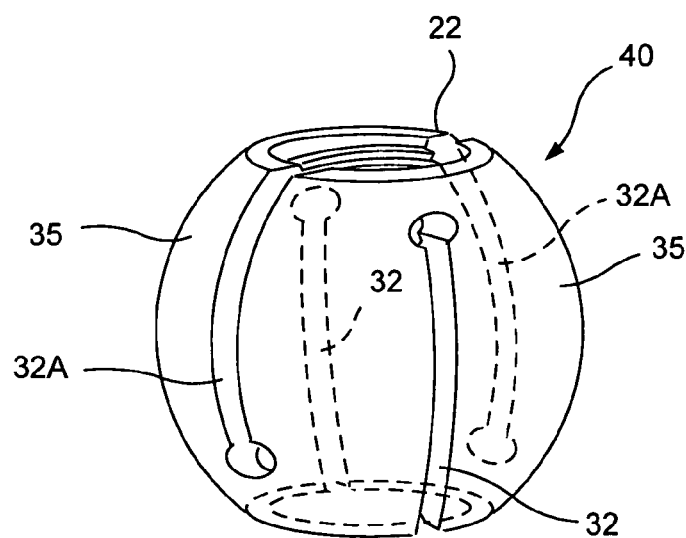
FIG. 10 is a diagrammatic perspective view of another embodiment of the bearing.

Referring to FIG. 10, therein is seen another embodiment of the bearing designated by numeral 40. In this embodiment, the bearing is provided with two sets of slots 32, 32A extending alternately from opposite ends of the bearing. In this way, the lever-like petals 35 extend from the top and bottom ends of the bearing and produce two zones of contact force couples which develop to lock the bearing in the hole 15 in the plate when the post is inserted into the bore 21 of the bearing.

FIG. 11 shows the bearing 17 of FIG. 8 in its initially loosely supported state in the plate 11 whereas FIG. 12 shows the bearing 17 after rotation in the plate 11 to its desired position.

Instead of using threads to engage the post in the bearing, the tapered end of the post can be made smooth and the post can be axially driven into the bore in the bearing to produce the expansion of the bearing.

FIGS. 13 and 14 illustrate a modification which employs means to prevent the bearing from spinning in the plate hole 15 when the post 16 is threadably advanced in the bore 21 in the bearing 17. In this regard, the plate is provided with one or more grooves or slots 50 extending from the hole 15. The bearing 17 is provided with radially extending tabs 51 at its upper end which fit into grooves 50. Thereafter, when the post 16 is advanced into the bore in the bearing, the bearing will be held fast in the plate hole. Although two diametrically opposed grooves 50 and tabs 51 have been shown, only a single groove and tab may be necessary. It is to be noted that although this drawing shows the grooves and locking tab at the top of the bearing and plate, these can also be placed at the lower portion of the bearing and plate without departing from the invention. The bearing can also be provided with a countersink 52 at the upper end of the bore so that when the post is fully advanced in the bore, the head of the post will be recessed in the bearing.

Another way of providing resistance of the bearing 17 from spinning in the plate hole 15, when the post 16 is advanced in the bore 21 in the bearing is to provide microtexturing in the form of microgrooves on the surface of the bearing. The microgrooves also improve torque resistance. Additionally, microgrooves can be provided on the surface of the hole 15.

Since the bearing and the plate hole have corresponding spherical surfaces closely conforming to one another, there is a problem of installing the bearing in the plate hole.

To avoid this problem, the slots in the bearing can be made sufficiently wide so that the bearing can be compressed to enable it to be inserted into the plate hole and thereafter resume its original spherical contour. The slots confer the flexibility of the petals of the bearing to enable the insertion to be made. This feature will be discussed in more detail later with reference to FIGS. 24–27.

Another way of inserting the bearing in the plate hole is to initially form the hole with a large cylindrical diameter at its top to enable insertion of the bearing. Thereafter a crimping or crushing pressure is applied to the plate around the top of the hole so that the hole deforms and retains the bearing in the hole while still permitting the bearing to be freely rotatable.

Still another way of installing the bearing is to cool the bearing in dry ice or liquid nitrogen and/or to heat the plate which will cause the bearing to shrink and the hole to expand allowing the bearing to be inserted into the hole. After the bearing and plate return to room temperature, the bearing will be rotatably retained in the hole.

Another problem to be resolved is to prevent the bearing from rotating 180° upside-down in the hole preventing proper installation of the post. In order to prevent this, the bearing is provided with a slight extension similar to tab 51 at one side to prevent it from turning upside down.

The embodiment illustrated in FIGS. 15-20 is constructed to restrain the bearing from spinning around a vertical axis during insertion of the post into the bore of the bearing and also to restrict angular travel of the bearing predominantly to a single plane.

Referring to FIGS. 15 and 16 therein is shown a radial tab 60 extending outwardly from the surface of the bearing 61. The bearing 61 is similar to the bearings previously described except that it is provided with a single longitudinal slot 62 extending along the entire length of the bearing to form a split bearing which can be outwardly expanded when the post (not shown) is inserted into the hole 63 in the bearing 61. The bearing can also be constructed with slots as shown in any of the previous FIGS. or as the simple truncated spherical bearing with a single longitudinal slot as shown. The feature disclosed in this embodiment is the means to prevent spinning and restrict angular travel of the bearing. This means is comprised of the tab 60 which engages in a groove 64 which extends outwardly from the hole 65 in plate 66 along the thickness of the plate. As seen in FIG. 18, the arrangement of the tab 60 and groove 64 forms a key and keyway type of engagement which limits angular travel around the vertical axis 67 of the bearing and permits angular rotation of the bearing in plane A—A with capability of a small amount of side-to-side movement based on an oversize of the groove 64 relative to tab 60 as seen in FIG. 18.

FIGS. 19 and 20 show the bearing in an angularly rotated position in the hole 65 in plate 66 where the bearing has been turned to the side (clockwise) to the extent permitted by the travel of the tab 60 in the oversize groove 64.

The use of a single tab as shown in FIGS. 15 and 16 has the disadvantage that the bearing tends to rotate around the tab as the post is inserted, generating a large shearing force across the tab. This can be overcome by placing a second tab on the bearing and a second groove in the hole on the opposite side (not shown).

FIGS. 21 and 22 show a bearing 71 according to a modified embodiment which limits angular movement of the bearing 71 in the plate 11. The bearing 71 is provided with opposite flat sides 72 extending from top to bottom of the bearing, although any non-circular cross-sectional outline would serve an equivalent function. The plate 11 has a hole 73 with a shape conforming to the outer surface of the bearing. Namely, the hole 73 has flat sides 74 facing the flat sides 72 of the bearing and the remainder of the surface of the hole is spherical and conforms to the surface of the bearing. Accordingly, angular rotation of the bearing is limited as shown in FIG. 23. The magnitude of angular movement is a function of the clearance at the flat sides of the bearing and the hole. The embodiment also provides resistance of the bearing from spinning when the post is screwed into the hole in the bearing. In the embodiment illustrated in FIG. 22 the bearing is free to rotate angularly in a vertical plane C—C.

FIGS. 24–28 show another embodiment designed to reduce stress and increase the resistance to fatigue failure and cracking of the bearing.

Referring to FIGS. 24–27 therein is shown a truncated bearing 100 in which the slot 101 is wider at the lower end 102 than the upper end 103. The slot ends in an area of enlarged radius 104 in order to provide stress relief from cracking at the top of the slot. The bearing has a spherical outer surface in its at rest state and has a central threaded bore 105 for insertion of a post with a threaded shank. The outer diameter of the bearing 100 is slightly larger than the diameter of the hole 201 in the plate 200.

FIG. 25 shows the bearing after it has been compressed. The outer surface of the bearing 102 has been reduced in size allowing it to be inserted in the hole 201 in plate 200. In addition, the compression has caused the central threaded bore 105 to become inclined, with a smaller width at the bottom than at the top of the hole. Finally, the compression has pre-stressed a bridge or solid region 106 of the bearing above the slot 101 by bending it up causing slight compression on the lower surface of the bridge and tension on the upper surface of the bridge.

FIG. 26 shows superimposed the unstressed bearing 100 over the pre-stressed bearing 107 with the reduction in cross-sectional diameter.

Figure 27:
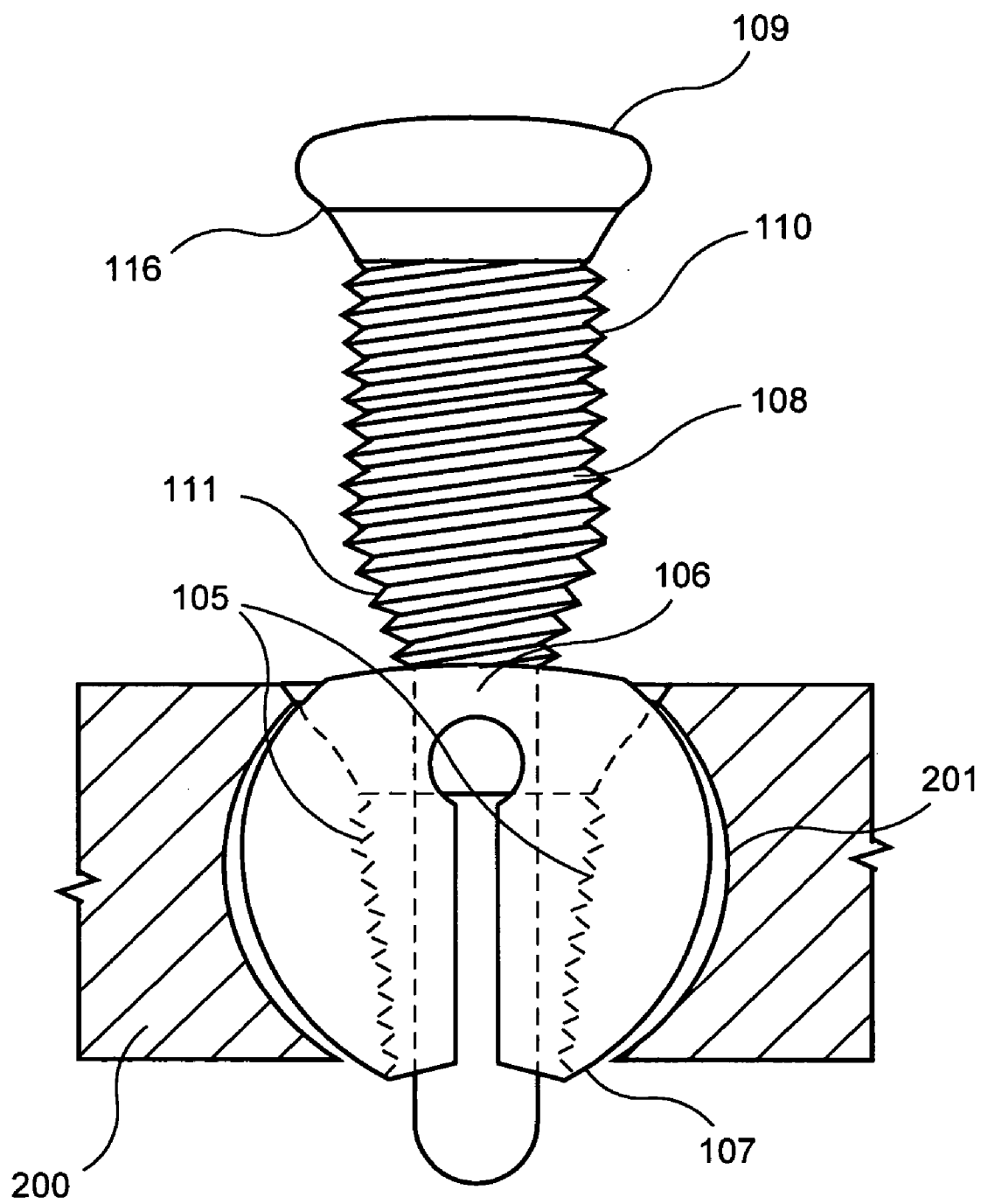
FIG. 27 shows the bearing of FIG. 25 after it has been inserted into a bone fixation plate and before seating of a post in the bearing.

FIG. 27 shows the post 108 before it is seated into the pre-stressed bearing 107 which has been placed in the hole 201 in plate 200. The upper portion of the post has a lower tapered zone 111 and an upper threaded zone 110 that matches the width of the upper portion of the threaded bore 105 of bearing 107. Prior to expansion, the bridge 106 above the slot is pre-stressed.

FIG. 28 shows expansion of the bearing 100 towards its original shape as the post 108 is inserted. The bend in bridge 106 above the slot is close to its original at-rest state when the bearing is expanded, reducing the stresses in this region when the bearing is expanded. This pre-stressed bearing design can be used with any of the other previously described slotted bearing designs.

Figure 29:
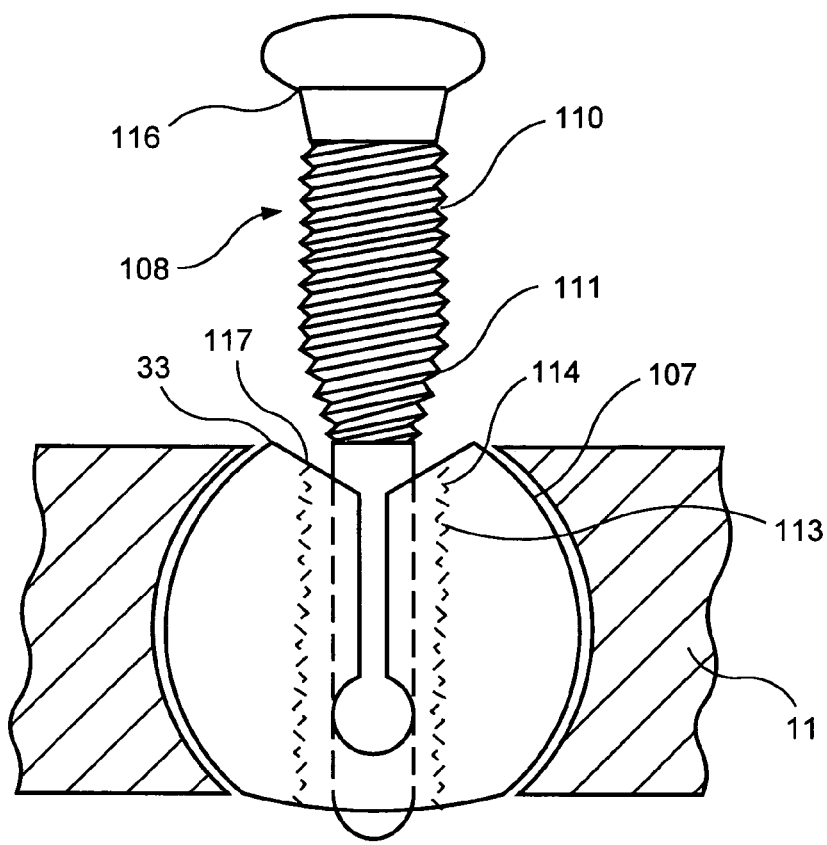
FIG. 29 is a diagrammatic elevation view of another embodiment according to the invention, in which the post has not yet been inserted into the bearing.
Figure 30:
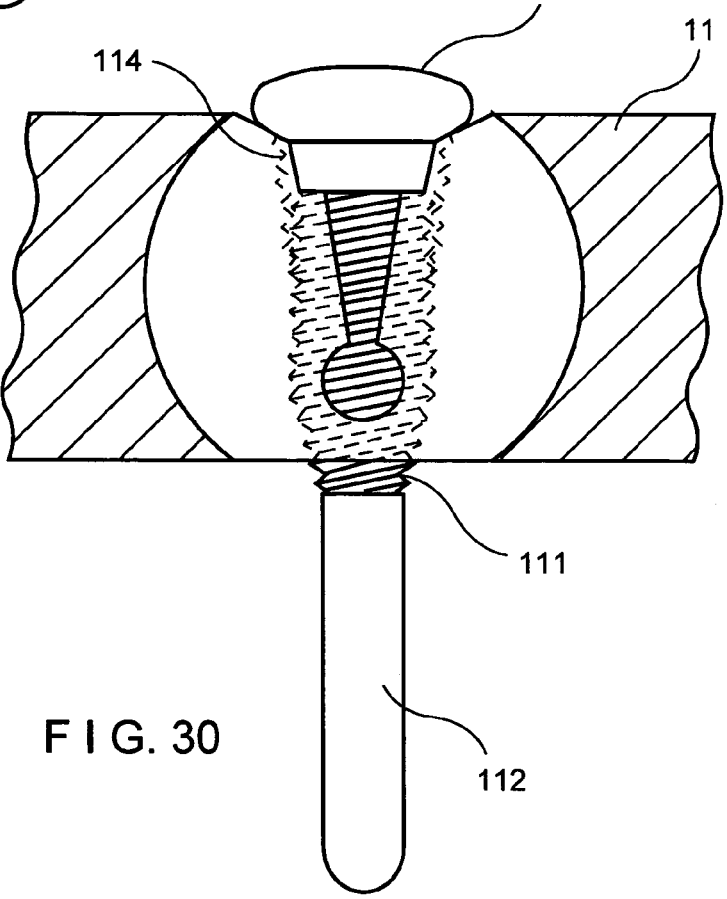
FIG. 30 shows the embodiment of FIG. 29 in which the post has been inserted into the bearing

FIGS. 29 and 30 show another embodiment in which the bearing 107 is similar to that shown in FIGS. 24–28. The plate 11 in which the bearing is seated is shown in FIGS. 29 and 30. The post 108 has a smooth cylindrical portion 112 adapted for insertion into a bone fragment (not shown). The cylindrical portion 112 can also be threaded to increase engagement with the bone fragment. The post is provided with the threaded portion 110 extending upwardly from the cylindrical portion 112. The threaded portion 110 is tapered to facilitate entry into a widened end 114 at the top of the threaded bore 113 in bearing 107. The tapered section 111 merges with a cylindrical threaded portion 110 which threadably engages in the threaded bore 113 in the bearing 107. A head 109 is formed at the top of the upper threaded portion 110 of the post and the head 109 has a lower bevel surface 116 which conforms to a bevel surface 117 at the upper end of the bore 113. When the post 108 is fully seated in the bearing, the head of the post causes the open ends 33 of the petals 35 to expand and bite into the wall of the hole in the plate (not shown). This arrangement for expansion of the bearing can be used with any of the previously described embodiments in which the post is inserted from the open end of the bearing. The bevel surface 116 can be formed with a taper having a slight mismatch with the taper of the bevel surface 117 at the top of the bearing 107 to form a Morse taper to lock the post in the bearing when fully seated.

Figure 31:
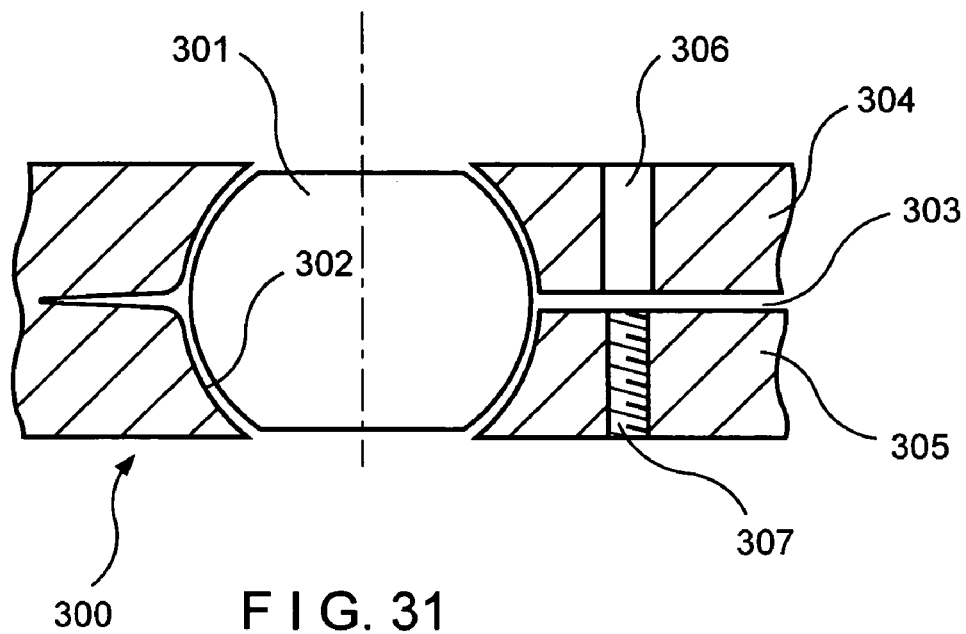
FIG. 31 is a diagrammatic elevational view of another embodiment according to the invention in which the bearing is free for rotation.
Figure 32:
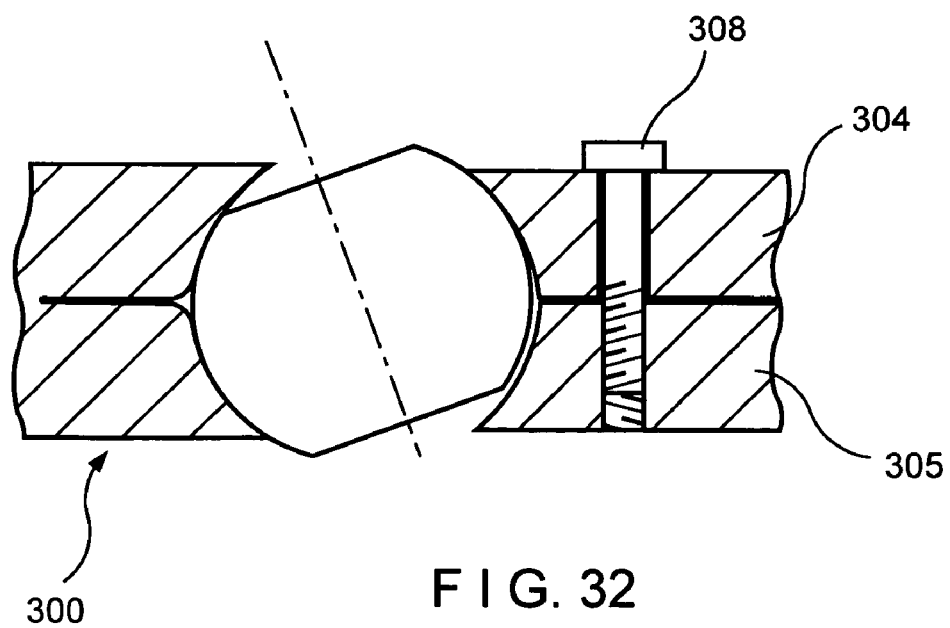
FIG. 32 shows the embodiment of FIG. 31 in which the bearing has been rotated and locked in position in the plate.

Referring to FIGS. 31 and 32, therein is seen plate 300 with bearing 301 in hole 302. In FIG. 29, the bearing is rotatable in the hole 302 in plate 300 and the post is not shown. The plate 300 is formed with a horizontal slot 303, that is partially cut horizontally in the plate to form upper plate segment 304, and lower plate segment 305, with a separation between the two. The plate segments 304, 305 are formed with aligned holes 306, 307 respectively. The hole 306 is smooth and the hole 307 is threaded. In this embodiment, the bearing 301 does not have to be split or expandible. After the post (not shown) has been inserted into the angularly adjusted bearing and into the associated bone fragment, the bearing 301 is locked in place by inserting threaded fastener 308 in holes 306 and 307 to clamp and tighten the plate segments 304, 305 against the bearing 301 as shown in FIG. 32. This will produce compressive forces acting on the bearing in the upper hemisphere at the right and the lower hemisphere at the left to produce non-uniformly acting forces on the bearing to develop torque resistance to forces applied to the post.

Instead of being horizontal, the slot 303 can be oblique or even vertical. Instead of extending partially through the plate, the slot can extend completely through the plate and the segments of the plate can be hinged or screwed together. Instead of using a threaded fastener 308 to compress the two segments of the plate, any connecting fastener such as a clip or rivet can be used.

In addition, the bearing 301 may have one or more partial or complete slots so that as the two segments of the plate are compressed against the bearing, the bearing compresses against the post so as to lock the post to the bearing.

What is claimed is:

1. A fracture fixation system comprising:
   a fixation plate adapted for being secured to a bone fragment on one side of a one fracture,
   an intermediate member loosely supported in a hole in said plate for angular adjustment movement therein, and
   a bone fastener member insertable into a bore in said intermediate member and being angularly adjustable by angular movement of the intermediate member,
   said bone fastener member being adapted for engagement with a bone fragment on an opposite side of the bone fracture,
   means acting between said bone fastener member and said intermediate member for fixedly securing the intermediate member in the plate and the bone fastener member in the intermediate member in an angularly adjusted position whereby the bone fastener member can provide fracture fixation,
   said bone fastener member and said intermediate member cooperatively acting to produce distribution of reactive forces acting non-uniformly against a wall of the hole in the plate to resist torque applied to the bone fastener member by the associated bone fragment.

2. The fracture fixation system of claim 1, wherein said intermediate member and said hole in the plate are configured to produce separate zones of contact between the intermediate member and the plate across the thickness of the plate whereby to obtain said non-uniform distribution of reactive forces.

3. The fracture fixation system of claim 2, wherein said contact between the intermediate member the plate is restricted to upper and lower regions of the intermediate member.

4. The fracture fixation system of claim 3, wherein said bore and said upper end portion of the post are threaded for threaded engagement therebetween.

5. The fracture fixation system of claim 4, wherein the upper end portion of the post is oversized relative to the bore in the bearing member to produce the expansion of the bearing member when the post is threadably advanced in said bore.

6. The fracture fixation system of claim 2, wherein said bone fastener member comprises a post having a lower end portion adapted for being secured to the respective bone fragment, said intermediate member comprising a bearing member which is outwardly expandible to be fixedly secured in the hole in the plate, said post having an upper end portion which engages in the bore in the bearing member, said means for fixedly securing the bearing in the plate and the post in the bearing is formed between the upper end portion of the post and the bore in the bearing member to cause the bearing member to expand and become locked in the hole when the upper end portion of the post is advanced in said bore in said bearing member, said means for producing the non-uniform distribution of forces between the bearing member and the plate being achieved by one or more slots provided in said bearing members.

7. The fracture fixation system of claim 6, wherein a plurality of said slots are provided and extend partially along the length of the bearing member, said slots extending from one end of the bearing member to define lever-like petals around the bearing member which are opened when the post is advanced in the bearing member to develop compressive forces between the bearing member and the plate at top and bottom ends of the hole to produce said force couple to lock the bearing member in the hole.

8. The fracture fixation system of claim 7, wherein the slots have terminal ends in the bearing member which are enlarged to provide stress relief and to promote flexibility of said lever-like petals.

9. The fracture fixation system of claim 7, wherein said lever-like petals act as cantilever beams, when opened by advancement of the post in the bearing member so that tips of the cantilever beams produce compression against the plate at the associated end of the hole.

10. The fracture fixation system of claim 9, wherein said one end of the bearing member is the upper end thereof in proximity to an upper surface of the plate.

11. The fracture fixation system of claim 10, wherein four of said slots are provided in the bearing member at equal circumferential spacing therearound to form four said lever-like petals.

12. The fracture fixation system of claim 11, wherein said slots extend from opposite ends of the bearing member in alternation to provide two sets of said petals respectively secured to opposite ends of said bearing member.

13. The fracture fixation system of claim 6, wherein said bearing member has an outer spherical surface and said hole has a corresponding spherical surface.

14. The fracture fixation system of claim 6, in which said bearing member is of predominately polyhedral form with apices that define a surface of predominately spherical shape.

15. The fracture fixation system of claim 6, in which the outer surface of either the bearing member or the surface of the hole is substantially textured to create frictional forces between the bearing member and the hole as the bearing member expands.

16. The fracture fixation system of claim 6, comprising a key arrangement between said bearing member and the hole in the plate to oppose relative latitudinal rotation therebetween while permitting relative longitudinal rotation therebetween.

17. The fracture fixation system of claim 16, wherein said key arrangement comprises a key on the bearing member or hole and a corresponding groove for the key in the hole or bearing member.

18. The fracture fixation system of claim 16, wherein said key arrangement comprises a key on the upper or lower end portion of the post and a groove in said plate at a corresponding upper or lower end of said hole in a position to receive said key as the head is advanced in said bore in the bearing member.

19. The fracture fixation system of claim 16, wherein said key arrangement limits insertion angle of the post predominantly to a single plane.

20. The fracture fixation system of claim 6, in which the plate has upper and lower surfaces at least one of which is countersunk at the hole.

21. The fracture fixation system of claim 20, wherein said conical surface is threaded.

22. The fracture fixation system of claim 6, in which the hole in the plate is inclined to allow an asymmetric range of post insertion angles.

23. The fracture fixation system of claim 6, in which the hole is shaped to prevent the bearing member from exiting from the hole.

24. The fracture fixation system of claim 6, wherein said upper end portion of the post has a conical surface to engage the bore in the bearing member.

25. The fracture fixation system of claim 1, wherein the intermediate member and the plate are configured to prevent contact between the intermediate member and the plate in an equatorial region of the intermediate member when the intermediate member is expanded.

26. The fracture fixation system of claim 1, wherein said distribution of reactive forces acting non-uniformly against the wall of the hole in the plate produces a force couple.

27. The fracture fixation system of claim 26, wherein said intermediate member and said hole in said plate are constructed and arranged to constitute a means for producing a force couple to resist the torque applied to the bone fastener member.

28. The fracture fixation system of claim 1, wherein said plate is provided with a slot dividing the plate into two segments, said system further comprising means for compressing said segments together to clamp the segments against said intermediate member to produce said distribution of reactive forces acting non-uniformly against the hole in the plate.

29. The combination comprising a post adapted for being secured to a bone fragment on one side of a bone fracture and a bearing for securing the post in an adjusted angular position in a hole in a plate which is adapted for being secured to another bone fragment on an opposite side of the fracture and thereby provide fracture fixation, said bearing having an outer surface defining a contour of predominantly spherical shape adapted to rotate in a hole of predominantly spherical shape in said plate, said bearing having a central bore in which the post can extend and be angularly adjustable by rotation of the bearing in the hole in the plate, said bearing being provided with slot means therein to enable radial expansion of the bearing when the post is axially advanced in the bore in the bearing and means for producing reactive forces between the surface of the bearing and the surface of the hole in the plate which produce a non-uniform force distribution between the bearing and the plate to resist torque applied to the post due to bone fragment drift.

30. The combination of claim 29, wherein said slot means comprises a plurality of slots extending from one end of the bearing partially along the length of the bearing to define lever-like petals around said bearing, said means for producing said non-uniform force distribution comprising means between the post and the bearing to open said lever-like petals when the post is axially advanced in said bore to cause tips of the lever-like petals to move outwardly and bear against the plate at one end of the hole while the bearing bears against the plate at the other end of the hole to develop said non-uniform force distribution.

31. The combination of claim 30, wherein said bearing has an inner end in proximity to a lower surface of the plate and an outer end in proximity to an upper surface of the plate, the post passing through the bore from the outer end to the inner end, said slots in the bearing extending from the outer end towards the inner end.

32. The combination of claim 31, wherein the slots have ends which terminate in said bearing and are provided with enlargements at said ends of the slots of a size larger than a width of said slots to provide stress relief for the slots and promote expansion of said lever-like petals.

33. The combination of claim 32, wherein said means to expand the lever-like petals comprises a tapered portion on said post.

34. The combination of claim 33, wherein the post and bore in the bearing are threaded and threadably engaged when the post is advanced in the bone of the bearing.

35. The combination of claim 33, comprising an enlargement at said upper end of the post to limit insertion in the hole in said bearing.

36. The combination of claim 31, wherein said plate includes means for preventing said bearing member from turning upside-down in said hole in the plate.

37. The combination of claim 29, wherein said place has one or more grooves extending radially from said hole and said bearing includes one or more projections which engage in a respective said groove in the plate to limit relative rotation between the bearing and the plate as the post is advanced in said bore.

38. The combination of claim 29, wherein said hole in the plate has a slightly enlarged middle region to restrict contact between the bearing and the plate to top and bottom portions of the plate for development of forces only thereat.

39. The combination of claim 29, wherein said non-uniform distribution of reactive forces produce a force couple when torque is applied to said post.

40. The combination of claim 29, wherein said means for producing non-uniform force distribution between the bearing and the plate comprises a slot dividing the plate into two segments and means for compressing said segments together to clamp the segments against said bearings to produce said non-uniform force distribution.

41. The combination of claim 29 further comprising means for limiting angular movement of the bearing in the hole in the plate.

42. The combination of claim 41, wherein the means for limiting angular movement of the bearing in the hole in the plate comprises a flattened side on the outer spherical surface of the bearing and a corresponding flattened side on the spherical surface of the hole facing the flattened side on the bearing surface.

43. The combination of claim 41, wherein the means for limiting angular movement of the bearing in the hole comprises a tab engaged in a groove, the tab being on one of the bearing or the plate and the groove being in the other of the plate or in the bearing.

44. The combination comprising a post adapted for being secured to a bone fragment on one side of a bone fracture and a bearing for securing the post in an adjusted angular position in a hole in a plate adapted for being secured to a further bone fragment on an opposite side of the bone fracture and thereby provide fracture fixation, said bearing having an outer surface defining a contour of predominantly spherical shape adapted to rotate in a hole of corresponding predominantly spherical shape in said plate, said bearing having a bore through which the post can extend and be angularly adjustable by rotation of the bearing in the hole in the plate, said post being axially advancable in said bore in the bearing to produce expansion of the bearing to secure the bearing in an angularly adjusted position of the post, said bearing and said hole being configured to provide means for producing compression forces between the bearing and the hole in the plate at upper and lower end regions of the bearing to develop a force couple to secure the bearing in the plate against rotation and resist torque applied to the bearing by forces applied to the post after fracture fixation.

45. The combination of claim 44, wherein said compression forces produced by said means at the upper and lower end regions of the bearing are non-colinear.

46. The combination of claim 45, wherein said means for producing said compression forces at the upper and lower end regions of the bearings also reduces contact between the outer surface of the bearing and the hole in the plate between said upper and lower end regions to diminish development of compression forces thereof.

47. The combination of claim 46, wherein said bearing has a longitudinal slot therein extending to said longitudinal bore in the body of the bearing.

48. The combination of claim 44, wherein said means which produces the compression forces at the upper and lower end regions of the bearings also reduces contact between the outer surface of the bearing and the hole in the plate between said upper and lower end regions to diminish development of compression forces thereat.

49. A fracture fixation system comprising:
a plate having one end portion adapted to be secured to a stable bone fragment of a fractured bone and an opposite end portion provided with a hole for passage therethrough of a post adapted for being secured into an unstable bone fragment of the fractured bone,
a bearing initially loosely seated in said hole for angular adjustment movement therein, said post extending through a bore in said bearing for being angularly adjusted with the bearing when the bearing is angularly moved in said hole,
said bearing being outwardly expandable to be locked in said hole after the post has reached an angularly adjusted position,
said post having a head portion which engages in the bore in said bearing, said head portion and said bore being configured to cause said bearing to expand and become locked in said hole when the head portion of the post is advanced in said bore in the bearing,
said bearing having one or more partial or complete slots therein extending through the bearing from the bore of the bearing to a surface of the bearing to allow expansion of the bearing and the development of compression forces acting against a surface of the hole in the plate,
said bearing having a tab that extends outward from the surface of the bearing
said hole in the plate having a groove of predetermined width that extends from an edge of the hole,
said groove and said tab being sized so that the tab fits within the groove and restrains said bearing from spinning around a vertical axis of the bearing during insertion of said post in the bearing.

50. The fracture fixation system of claim 49, wherein said groove and said tab are sized to restrict angular movement of the bearing in the hole in a single plane containing an axis of the hole.

51. The fracture fixation system of claim 50, wherein said groove is larger in size than said tab to allow a limited range of side to side movement of the bearing in the hole in addition to the angular movement of the bearing in the hole in the single plane containing the axis of the hole.

52. The fracture fixation system of claim 49, wherein said bearing is provided with a single one of said slots extending radially outwards from said bore through the bearing from top to bottom thereof.

53. The fracture fixation system of claim 49, wherein said bearing is provided with a plurality of said slots extending longitudinally in the bearing partially along the length of the bearing from one end of the bearing towards the opposite end of the bearing.

54. The combination comprising a post adapted for being secured to a bone fragment on one side of a bone fracture and a bearing for securing the post in an adjusted angular position in a hole in a plate which is adapted for being secured to another bone fragment on an opposite side of the fracture and thereby provide fracture fixation, said bearing having an outer surface defining a contour of spherical shape adapted to rotate in a hole of spherical shape in said plate, said bearing having a central bore in which the post can extend and be angularly adjustable by rotation of the bearing in the hole in the plate, and means for producing forces between said outer surface of the bearing and the surface of the hole in the plate which produce a non-uniform force distribution between the bearing and the plate to resist torque applied to the post due to bone fragment drift, said means comprising a slot in said plate dividing the plate into two segments and means for compressing the plate segments together to produce said non-uniform force distribution across the bearing by inequality of forces acting between said plate segments and said bearing.

55. Apparatus for achieving fracture fixation comprising:
a plate adapted for being secured to a bone,
a bearing rotatably mounted in a hole in the plate, and
a post insertable in an upper end of the bearing to extend through the bearing and project from a lower end of the bearing for engaging another bone whereby to provide fracture fixation of the bones,
said post including a distal portion which projects from the bearing for engaging said another bone, and a proximal portion which engages said bearing,
said bearing being provided with a longitudinal bore having a bevel at said upper end of the bearing, said longitudinal bore being threaded up to said bevel,
said post including a head at a proximal end thereof, a tapered section extending from said head and a threaded section for threadably engaging the threaded longitudinal bore in said bearing,
said bearing having a longitudinal slot extending from one of said ends of the bearing along the length of the bearing towards the other of the ends of the bearing to provide radial flexibility of the bearing,
said tapered section of the post being oversized relative to said bore in the bearing to radially expand the bearing when the post is threadably advanced in the bearing to seat the angularly adjusted position therein.

56. The apparatus of claim 55, wherein said distal portion of the post is smooth.

57. The apparatus of claim 55, wherein said head on the post has an undersurface with a bevel to engage the bore at the upper end of the bearing when the post is seated in the bearing.

58. The apparatus of claim 57, wherein the bevel in the bearing and the bevel on the head of the post have different angles of taper to produce an interference fit therebetween when the post is seated in the bearing to prevent the post from locking out of the bearing.

59. The apparatus of claim 58, wherein said slot in the bearing extends from the bevel at the upper end of the bearing.

60. The apparatus of claim 55, wherein the bearing and the hole have predominantly corresponding spherical surfaces.

61. The apparatus of claim 55 wherein said threaded section on the post is tapered at a lower end of the threaded section to facilitate entry into the threaded longitudinal bore in the bearing.

62. A fracture fixation system comprising:
a plate having one end portion adapted to be secured to a stable bone fragment of a fractured bone and an opposite end portion provided with a hole for passage therethrough of a post adapted for being secured into an unstable bone fragment of the fractured bone,
a bearing seated in said hole for angular adjustment movement therein, said post extending through a bore in said bearing for being angularly adjusted with the bearing when the bearing is angularly moved in said hole,
said post having a head portion which engages in the bore in said bearing,
and a tab and groove engagement between the bearing and the plate in which said tab and groove are sized so that the tab fits within the groove and restrains said bearing from spinning around a vertical axis of the bearing during insertion of said post in the bearing.

63. A method of securing a post in an angulated position in a bearing in turn secured in a hole in a plate, said method comprising the steps of:
providing a plate with a hole of predominantly spherical shape,
providing a bearing with an outer surface of predominantly spherical shape corresponding to the shape of the hole but slightly oversized with respect thereto,
providing a threaded longitudinal bore in the bearing,
forming a plurality of longitudinal slots in the bearing extending from one end of the bearing partially along the length of the bearing towards the other end of the bearing to form a plurality of petals around the bearing which provide radial compressability of the bearing,
inserting the bearing while compressed, into the hole in the plate thus allowing the bearing to expand and engage the plate while being angularly adjustable therein,
threadably advancing a post into the longitudinal bore in the bearing so that a distal end of the post extends beyond the bearing and a head on a proximal end of the post is seated at an upper end of the bearing, and
providing an interference fit between the post and the bore in the bearing so that when the post is threadably advanced in the bore in the bearing and the head of the post is seated on the bearing, the petals of the bearing are expanded to tightly engage the hole in the bearing and secure the bearing in an angularly adjusted portion in the hole.

64. The method of claim 63 comprising providing a bevel at the upper end of the bore in the bearing and a bevel on an underside of the head on the post, the bevels having different taper angles such that when the head is seated an interference will be formed between the bevels to oppose backing out of the post from the bore.

65. A fixation system adapted for securing bone members together, said fixation system comprising:
a fixation plate adapted for extending across a plurality of bone members which are to be secured together,
a plurality of bone fasteners for securing said fixation plate to the bone members, and
at least one intermediate member disposed in a hole in said plate to enable a respective said bone fastener to be angularly adjustable in said plate to permit the respective bone fastener to enter the respective bone member at a selected angle whereafter the intermediate member becomes secured in said plate at the selected angle, and
means acting between said bone fastener and said intermediate member for fixedly securing the intermediate member in the hole in the plate and the bone fastener in the intermediate member at said selected angle,
said bone fastener and said intermediate member cooperatively acting to produce distribution of reactive forces acting non-uniformly against a wall of the hole in the plate to resist torque applied to the bone fastener by the associated bone.

66. The fixation system of claim 65, wherein said intermediate member and said hole in the plate are configured to produce separate zones of contact between the intermediate member and the plate across the thickness of the plate whereby to obtain said non-uniform distribution of reactive forces.

67. The fracture fixation system of claim 66, wherein said contact between the intermediate member and the plate is restricted to upper and lower regions of the intermediate member.

68. The fixation system of claim 67, wherein said intermediate member and said hole in said plate are constructed and arranged to constitute a means for producing a force couple to resist the torque applied to the bone fastener.

69. The fixation system of claim 65, wherein said bone fastener has a lower end portion adapted for being secured to the respective bone, said intermediate member comprising a bearing member which is outwardly expandible to be fixedly secured in the hole in the plate, said bone fastener having an upper end portion which engages in a bore in the bearing member, said means for fixedly securing the bearing in the plate and the bone fastener in the bearing is formed between the upper end portion of the bone fastener and the bore in the bearing member to cause the bearing member to expand and become locked in the hole when the upper end portion of the bone fastener is advanced in said bore in said bearing member, said means for producing the non-uniform distribution of forces between the bearing member and the plate being achieved by one or more slots provided in said bearing members.

70. The fixation system of claim 69, wherein a plurality of said slots are provided and extend partially along the length of the bearing member, said slots extending from one end of the bearing member to define lever-like petals around the bearing member which are opened when the bone fastener is advanced in the bearing member to develop compressive forces between the bearing member and the plate at top and bottom ends of the hole to produce a force couple to lock the bearing member in the hole.

71. A fixation system adapted for securing bone members together, said fixation system comprising:

a bone screw adapted for being secured to a bone member and a bearing for securing the bone screw in an adjusted angular position in a hole in a plate which is adapted for being secured to another bone member and thereby secure the bone members together, said bearing having an outer surface defining a contour of predominantly spherical shape adapted to rotate in a hole of predominantly spherical shape in said plate, said bearing having a central bore in which the bone screw can extend and be angularly adjustable by rotation of the bearing in the hole in the plate, said bearing being provided with slot means therein to enable radial expansion of the bearing when the bone screw is axially advanced in the bore in the bearing and means for producing reactive forces between the surface of the bearing and the surface of the hole in the plate which produce a non-uniform force distribution between the bearing and the plate to develop a force couple to resist torque applied to the bone screw due to drift of the bone member, said slot means comprising a plurality of slots extending from one end of the bearing partially along the length of the bearing to define lever-like petals around said bearing, said means for producing said non-uniform force distribution comprising means between the bone screw and the bearing to open said lever-like petals when the bone screw is axially advanced in said bore to cause tips of the lever-like petals to move outwardly and bear against the plate at one end of the hole while the bearing bears against the plate at the other end of the hole to develop said non-uniform force distribution.

72. The fixation system of claim 71, further comprising means for opposing spinning movement of the bearing in the hole in the plate as the bone screw is advanced in the hole in the bearing.

73. The fixation system of claim 71, wherein said bearing has an inner end in proximity to a lower surface of the plate and an outer end in proximity to an upper surface of the plate, the bone screw passing through the bore from the outer end to the inner end, said slots in the bearing extending from the outer end towards the inner end, said slots having ends which terminate in said bearing and are provided with enlargements at said ends of the slots of a size larger than a width of said slots to provide stress relief for the slots and promote expansion of said lever-like petals.

74. The combination comprising a bone screw adapted for being secured to a bone member and a bearing for securing the bone screw in an adjusted angular position in a hole in a plate which is adapted for being secured to another bone member and thereby secure the bone members together, said bearing having an outer surface defining a contour of predominantly spherical shape adapted to rotate in a hole of predominantly spherical shape in said plate, said bearing having a central bore in which the bone screw can extend and be angularly adjustable by rotation of the bearing in the hole in the plate, said bearing being provided with slot means therein to enable radial expansion of the bearing when the bone screw is axially advanced in the bore in the bearing and means for producing reactive forces between the surface of the bearing and the surface of the hole in the plate which produce a non-uniform force distribution between the bearing and the plate to develop a force couple to resist torque applied to the bone screw due to drift of the bone member, said means for producing a non-uniform force distribution between the bearing and the plate comprising a slot dividing the plate into two segments and means for compressing said segments together to clamp the segments against said bearing in spaced regions thereof to produce said non-uniform force distribution.

* * * * *